US012806388B2

(12) United States Patent
Mojarrad et al.

(10) Patent No.: US 12,806,388 B2
(45) Date of Patent: Nov. 24, 2026

(54) SWALLOWABLE DRUG DELIVERY DEVICES

(71) Applicant: AMGEN INC., Thousand Oaks, CA (US)

(72) Inventors: Mehran Mojarrad, Thousand Oaks, CA (US); Scott R. Gibson, Thousand Oaks, CA (US); Scott Castanon, Carlsbad, CA (US); Robert Eisele, Carlsbad, CA (US); Dylann Ceriani, San Diego, CA (US)

( * ) Notice: Subject to any disclaimer, the term of this patent is extended or adjusted under 35 U.S.C. 154(b) by 925 days.

(21) Appl. No.: 18/022,245

(22) PCT Filed: Sep. 2, 2021

(86) PCT No.: PCT/US2021/048805

§ 371 (c)(1),
(2) Date: Feb. 20, 2023

(87) PCT Pub. No.: WO2022/055779

PCT Pub. Date: Mar. 17, 2022

(65) Prior Publication Data

US 2023/0302264 A1 Sep. 28, 2023

Related U.S. Application Data

(60) Provisional application No. 63/076,291, filed on Sep. 9, 2020.

(51) Int. Cl.
*A61M 31/00* (2006.01)
*A61M 37/00* (2006.01)

(52) U.S. Cl.
CPC ...... *A61M 31/002* (2013.01); *A61M 37/0015* (2013.01)

(58) Field of Classification Search
CPC ........................ A61M 31/002; A61M 37/0015
(Continued)

(56) References Cited

U.S. PATENT DOCUMENTS 8,846,040 B2 * 9/2014 Imran ............. A61B 17/12136 424/134.1
2012/0165793 A1 6/2012 Ortiz et al.
(Continued)

FOREIGN PATENT DOCUMENTS

EP 0174865 A2 3/1986
WO WO-2014159604 A1 10/2014

OTHER PUBLICATIONS

International Search Report and Written Opinion, issued to International Application No. PCT/US2021/048805, dated Feb. 14, 2022.

(Continued)

*Primary Examiner* — Phillip A Gray
(74) *Attorney, Agent, or Firm* — MARSHALL, GERSTEIN & BORUN LLP

(57) ABSTRACT

A swallowable drug delivery device includes a capsule and a tissue attachment member. The capsule may contain a drug and may be sized to pass through at least a portion of the gastrointestinal tract of a patient. The tissue attachment member may be coupled to the capsule. In an initial state, the tissue attachment member may allow the capsule to pass through the at least a portion of the gastrointestinal tract of the patient. In an activated state, the tissue attachment member is configured to at least selectively attach the capsule to a wall of the gastrointestinal tract of the patient. The tissue attachment member may be configured to change from the initial state to the activated state in response to an in vivo condition associated with a predetermined location in the gastrointestinal tract of the patient.

25 Claims, 11 Drawing Sheets

(58) Field of Classification Search
USPC ........................................................ 604/891.1
See application file for complete search history.

(56) References Cited

U.S. PATENT DOCUMENTS

| | | | | |
|---|---|---|---|---|
| 2013/0172694 | A1 | 7/2013 | Zou et al. | |
| 2015/0064241 | A1* | 3/2015 | Conrad ................ | A61B 5/0071 424/451 |

OTHER PUBLICATIONS

European Patent Application No. 21777916.4, Communication Pursuant to Article 94(3) EPC, dated Dec. 1, 2025.

* cited by examiner

SWALLOWABLE DRUG DELIVERY DEVICES

CROSS-REFERENCE TO RELATED APPLICATION

This is the United States national phase of International Patent Application No. PCT/US21/48805, filed Sep. 2, 2021, which claims priority to U.S. Provisional Patent Application No. 63/076,291, filed Sep. 9, 2020, the entire contents of each of which are hereby incorporated by reference herein.

FIELD OF DISCLOSURE

The present disclosure generally relates to drug delivery devices and, more particularly, swallowable drug delivery devices capable of delivering drugs in the gastrointestinal tract.

BACKGROUND

In recent years there has been an increase in the development of drugs for which an injection is the preferred or required administration route. Certain such drugs are not be suitable for oral administration due to complications related to chemical breakdown of active ingredients by enzymes in the gastrointestinal tract or liver, unpredictable or slow absorption of the drug by the gastrointestinal tract, irritation to the stomach or other organs included in the gastrointestinal tract, among other issues.

Various conventional administration techniques for injectable drugs involve piercing the patient's skin with a needle and subsequently injecting, via the needle, the drug subcutaneously, intravenously, etc. Oftentimes needle insertion can be painful or uncomfortable for the patient. Additionally, certain conventional injection techniques involve a risk of exposing the needle to contaminants in, for example, the ambient environment, as well as a risk for needlestick injuries. Moreover, in cases where a conventional syringe is used to inject a drug, it may be necessary to employ the services of a medical professional, which, in turn, reduces opportunities for home- or self-administration.

The present disclosure sets forth drug delivery devices embodying advantageous alternatives to existing drug delivery devices and that may address one or more of the challenges or needs mentioned herein, as well as provide other benefits and advantages.

SUMMARY

One aspect of the present disclosure provides a swallowable drug delivery device including a capsule and a tissue attachment member. The capsule may contain a drug and may be sized to move through at least a portion of a gastrointestinal tract of a patient. The tissue attachment member may be coupled to the capsule. In an initial state, the tissue attachment member may allow the capsule to move through the at least a portion of the gastrointestinal tract. In an activated state, the tissue attachment member may be configured to at least selectively attach the capsule to a wall of the gastrointestinal tract. The tissue attachment member may be configured to change from the initial state to the activated state in response to an in vivo condition associated with the gastrointestinal tract at a predetermined location.

Another aspect of the present disclosure provides a swallowable drug delivery device including a capsule, an adhesive, and a coating or shell. The capsule may contain a drug and may be sized to move through at least a portion of a gastrointestinal tract of a patient. The adhesive may be disposed on an exterior surface of the capsule and may be configured to at least selectively attach the capsule to a wall of the gastrointestinal tract. The coating or shell may cover at least a portion of the adhesive and may be configured to degrade to uncover the at least a portion of the adhesive in response to an in vivo condition associated with the gastrointestinal tract at a predetermined location.

An additional aspect of the present disclosure provides a system including a swallowable drug delivery device and an ex vivo device. The swallowable drug delivery deice may include a capsule and a tissue penetrating delivery member. The capsule may contain a drug and may be sized to move through at least a portion of a gastrointestinal tract of a patient. The tissue penetrating delivery member may have an interior passage in fluid communication or configured to be connected in fluid communication with the drug. The ex vivo device may be positionable adjacent to an abdomen of the patient. The ex vivo device may be configured to magnetically interact with the swallowable drug delivery device to position the swallowable drug delivery device against a wall of the gastrointestinal tract.

A further aspect of the present disclosure provides a swallowable drug delivery device including a capsule and a projectile. The capsule may be sized to move through at least a portion of a gastrointestinal tract of a patient. The projectile may contain a drug. In an initial state, the projectile may be disposed at least partially within the capsule. In an activated state, the projectile may move in a direction away from the capsule for insertion into a wall of the gastrointestinal tract.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to delivering drugs at various locations in the body of a patient, including at a predetermined or preferred location. Certain embodiments provide a swallowable or ingestible drug delivery device for delivering a drug within the gastrointestinal tract of the patient, including, for example, into a wall (e.g., inner wall) of the small intestine or other organ included in the gastrointestinal tract. It has been found that, in certain cases, delivering into the wall of the small intestine is advantageous due to the relative thinness of the mucosa of the small intestine as compared to other organs included in the gastrointestinal tract. In certain embodiments the swallowable device may be configured to at least selectively attach to the gastrointestinal tract at a predetermined location by passively or actively sensing an in vivo condition associated with the predetermined location. So configured, the swallowable drug delivery device may self-activate (e.g., autonomously activate) in response the in vivo condition to anchor itself and then deliver the drug at the predetermined location. Embodiments of the present disclosure may be useful for delivering drugs which are vulnerable to breakdown by enzymes and/or other degrading elements in the gastrointestinal tract and thus previously may have been limited to delivery via non-oral routes of administration such as, for example, subcutaneous and/or intravenous routes of administration. As used herein, the term "gastrointestinal tract" refers to the mouth, esophagus, stomach, small intestine, large intestine, and anus. As used herein, the term "intestinal" refers to the small intestine and the large intestine.

Figure 1A:
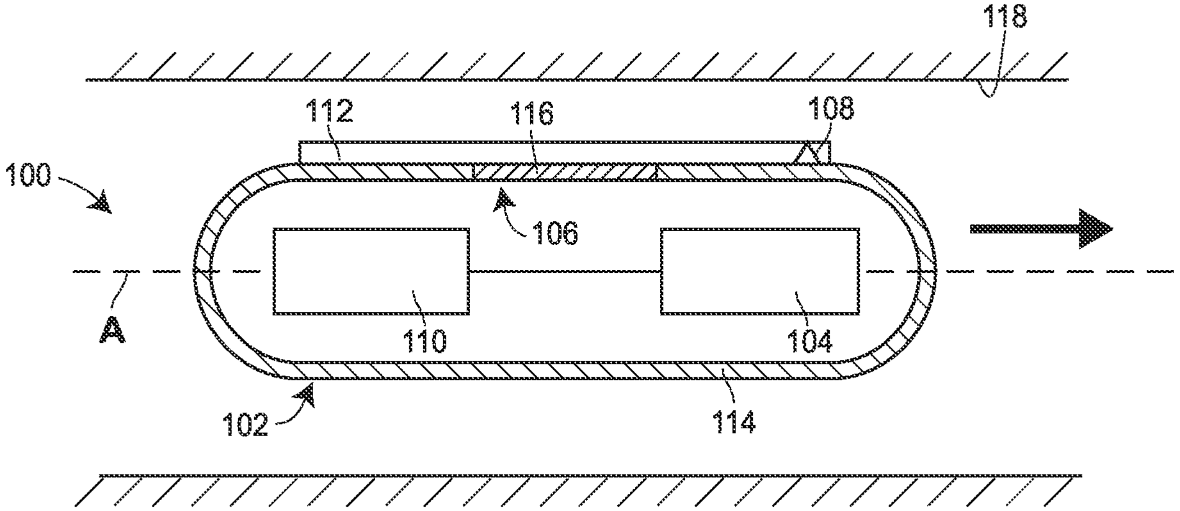
FIG. 1A is a schematic cross-sectional view of a swallowable drug delivery device according to an embodiment of the present disclosure, with a tissue attachment member in an initial state.
Figure 1B:
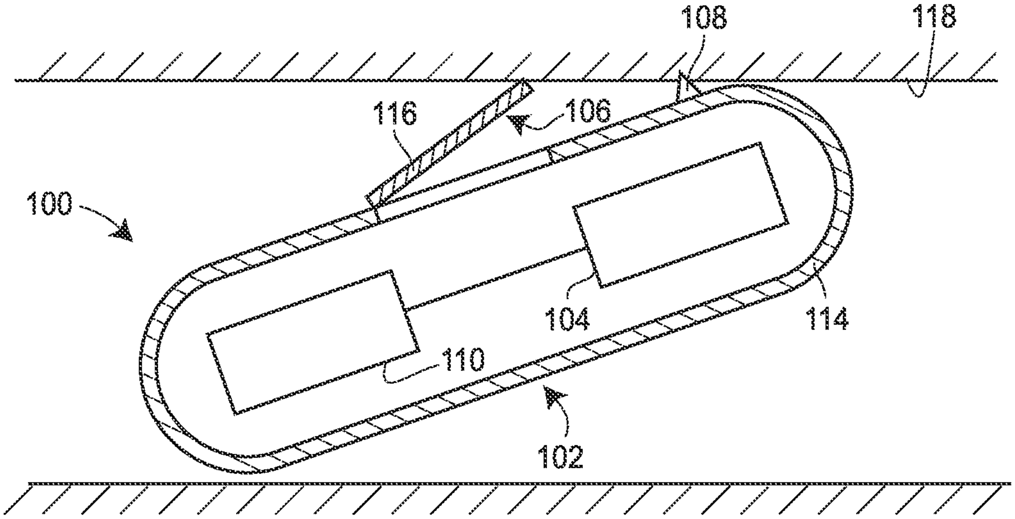
FIG. 1B is a schematic cross-sectional view of the swallowable drug delivery device in FIG. 1A, with the tissue attachment member in an activated state.

FIGS. 1A and 1B are schematic diagrams of a swallowable drug delivery device 100 according to an embodiment of the present disclosure. The swallowable drug delivery device 100 may include a number of components or subassemblies, such as a capsule 102, a reservoir 104 filled with a drug, a tissue attachment member 106, a tissue penetrating delivery member 108, an actuator 110, and a coating 112. The details of each of these components or subassemblies will be discussed below relative to a series of non-limiting examples.

The capsule 102 may have a wall 114 defining an interior space containing at least the reservoir 104 and the actuator 110. The capsule 102 may be sized to pass through some or all of the gastrointestinal tract, including, for example, passing through at least the mouth, esophagus, stomach, and an entry portion of the small intestine. To facilitate sliding through the esophagus, the capsule 102 may have, at least initially, an elongated shape corresponding to a cylinder with hemispherical ends, as seen in FIG. 1A. Other shapes are also possible including, for example, an egg-like or spherical shape. In some embodiments, the dimensions of the capsule 102 may be similar to the dimensions of a conventional medicinal pill or tablet intended to be swallowed by a person. In some embodiments, one or more openings may be formed in the wall 114 which communicate with the interior space of the capsule 102.

The capsule 102 may protect the drug payload from degradation by enzymes and other degrading elements in the gastrointestinal tract, at least during the time period between when the capsule 102 is swallowed by the patient and when the capsule 102 reaches a predetermined location within the gastrointestinal tract where delivery of the drug is intended. In some embodiments, the capsule 102 may be constructed of a material that degrades (e.g., dissolves, breaks apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 100 is swallowed by the patient) and/or exposure to enzyme(s), a concentration of enzyme(s), and/or a pH unique to a particular portion of the gastrointestinal tract such as the small intestine. In some embodiments, the predetermined amount of time may be selected so that the capsule 102 does not release the drug prior to the time when the swallowable drug delivery device 100 is expected to deliver the drug at a predetermined location such as, for example, within the small intestine.

The reservoir 104 may be disposed, entirely or partially, within the capsule 102 and may be filled, entirely or partially, with a drug. The drug may be, but is not limited to, various biologicals such as peptides, peptibodies, or antibodies. More examples of the drug are described below. The drug may be in a fluid or liquid form, although the disclosure is not limited to a particular state. Some or all of the wall(s) enclosing the drug in the reservoir 104 may correspond to the wall 114 of the capsule 102. Additionally or alternatively, some or all of the wall(s) enclosing the drug in the reservoir 104 may correspond to a wall 116 of the tissue attachment member 106. In some embodiments, the wall(s) enclosing the drug in the reservoir 104 may be physically distinct from the wall 114 of the capsule 102 and/or the wall 116 of the tissue attachment member 106. In some embodiments, the wall(s) enclosing the drug in the reservoir 104 may be rigid, flexible, or some combination of rigid and flexible. In some embodiments, the reservoir 104 may be a drug storage bladder having a flexible wall which can be compressed or otherwise deformed (e.g., elastically deformed) to expel the drug from the interior of the drug storage bladder.

The tissue penetrating delivery member 108 may be configured to deliver the drug from the reservoir 104 into an inner wall 118 of the gastrointestinal tract including, for example, into an inner wall of the small intestine. In some embodiments, the tissue penetrating delivery member 108 may be configured to deliver the drug directly into the mucosa or submucosa, including, for example, directly into and/or immediately adjacent to arteries, veins, and/or capillaries in the mucosa or submucosa. In some embodiments, the tissue penetrating delivery member 108 may be configured to deliver the drug at a depth beneath the surface of the inner wall 118 of the gastrointestinal tract in a range between approximately (e.g., ±10%) 150-250 μm, or at a depth beneath the surface of the inner wall 118 of the gastrointestinal tract in a range between approximately (e.g., ±10) 100-300 μm, or at a depth beneath the surface of the inner wall 118 of the gastrointestinal tract that is greater than approximately (e.g., ±10%) 100 μm, or at a depth beneath the surface of the inner wall 118 of the gastrointestinal tract that is greater than approximately (e.g., ±10%) 150 μm, or at a depth beneath the surface of the inner wall 118 of the gastrointestinal tract that is greater than approximately (e.g., ±10%) 200 μm. In embodiments where the preferred location for drug delivery is the small intestine, having a tissue penetrating delivery member 108 that is configured to deliver the drug at a depth beneath the surface of the inner wall of the small intestine in a range between approximately (e.g., ±10%) 150-250 μm may allow the tissue penetrating delivery member 108 to deliver the drug directly into or immediately adjacent to arteries, veins, and/or capillaries in the mucosa or submucosa.

In some embodiments, the tissue penetrating delivery member 108 may include a wall that defines an interior passage between a first end and a second end of the tissue penetrating delivery member 108. The wall may have a tapered region at the first end which, in some embodiments, may result in the first end having a point. Variously herein the first end of the tissue penetrating delivery member 108 is referred to as the pointed end of the tissue penetrating delivery member 108. One or more openings may be formed in the wall at the first end of the tissue penetrating delivery member 108 and may communicate with the interior passage of the tissue penetrating delivery member 108. The interior passage of the tissue penetrating delivery member 108 may, via the second end of the tissue penetrating delivery member 108, be connected in fluid communication or configured to be connected in fluid communication with the drug in the reservoir 104. During drug delivery, the drug may move out of the reservoir 104, then through the interior passage of the tissue penetrating delivery member 108, then out of the tissue penetrating delivery member 108 via the one or more openings in the first end of the tissue penetrating delivery member 108, and then directly into the inner wall 118 of the gastrointestinal tract.

The tissue penetrating delivery member 108 may take various forms depending on, for example, a preferred rate at which the drug is absorbed by the patient's tissue, a viscosity of the drug, a thickness of the inner wall of the gastrointestinal tract at the delivery location, among other factors. In some embodiments, the tissue penetrating delivery member 108 may be configured as one or more microneedles, one or more needles, one or more nozzles, or any combination thereof. The tissue penetrating delivery member 108 may be made of a relatively rigid material such as metal and/or certain polymers. Furthermore, in some embodiments, the material used to construct the tissue penetrating delivery member 108 may degrade (e.g., dissolve, break apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 100 is swallowed by the patient) and/or exposure to enzyme(s), a concentration of enzyme(s), and/or a pH unique to a particular portion of the gastrointestinal tract such as the small intestine. A single tissue penetrating deliver member 108 may be included as seen in FIGS. 1A and 1B; or multiple tissue penetrating deliver members 108 may be included.

The tissue penetrating delivery member 108 may be coupled to the wall 114 of the capsule 102 with the first end of the tissue penetrating delivery member 108 extending outwardly from the wall 114 of the capsule 102, as illustrated in FIGS. 1A and 1B. Additionally or alternatively, the tissue penetrating delivery member 108 may be coupled to the wall 116 of the tissue attachment member 106 with the first end of the tissue penetrating delivery member 108 extending outwardly from the wall 116 of the tissue attachment member 106.

In some embodiments, the tissue penetrating delivery member 108 may be fixed (i.e., immoveable) relative to the wall 114 of the capsule 102 and/or the wall 116 of the tissue attachment member 106. In alternative embodiments, the tissue penetrating delivery member 108 may be moveable relative to the wall 114 of the capsule 102 and/or the wall 116 of the tissue attachment member 106. In such alternative embodiments, the tissue penetrating delivery member 108 may be actuated to move from an initial position, where the first end of the tissue penetrating delivery member 108 is disposed within the capsule 102 or the tissue attachment member 106, to a delivery position, where the first end of the tissue penetrating delivery member 108 is disposed through the wall 114 of the capsule 102 or the wall 116 of the tissue attachment member 106 for insertion into the inner wall 118 of the gastrointestinal tract.

In some embodiments, the tissue penetrating delivery member 108 may be omitted. In certain such embodiments, the wall 114 of the capsule 102 and/or the wall 116 of the tissue attachment member 106 may have one or more openings which are configured to deliver the drug into a lumen of the gastrointestinal tract at a predetermined location. Alternatively or additionally, the wall 114 of the capsule 102 and/or the wall 116 of the tissue attachment member 106 may degrade (e.g., dissolve, break apart into smaller pieces, etc.) in order to release the drug into a lumen of the gastrointestinal tract at a predetermined location. This degradation may occur as a result of exposure to enzyme(s) and/or other degrading element(s) in the gastrointestinal tract, including, for example, after exposure to such element(s) for a predetermined amount of time (for example, 8-12 hours after the swallowable drug delivery device 100 is swallowed by the patient) and/or exposure to enzyme(s), a concentration of enzyme(s), and/or a pH unique to a particular portion of the gastrointestinal tract such as the small intestine. In some embodiments, the swallowable drug delivery device 100 may be configured to deliver the drug via any combination of: the tissue penetrating delivery member(s) 108; opening(s) in the wall 114 of the capsule 102; opening(s) in the wall 116 of the tissue attachment member 106; degradation of the wall 114 of the capsule 102; and degradation of the wall 116 of the tissue attachment member 106.

In general terms, the tissue attachment member 106 may function as an anchor for stationarily or substantially stationarily positioning the capsule 102 in the gastrointestinal tract at a predetermined (e.g., preselected, targeted, chosen, preferred, etc.) location. The tissue attachment member 106 may have at least two states: an initial state (FIG. 1A) wherein the tissue attachment member 106 allows the capsule 102 to pass freely through at least a portion of the gastrointestinal tract or at least does not actively impede passage of the capsule 106 through the at least a portion of the gastrointestinal tract; and an activated state (FIG. 1B) wherein the tissue attachment member 106 temporarily or permanently attaches the capsule 102 to the inner wall 118 of the gastrointestinal tract such as the small intestine. The attachment may be permanent in the sense that the tissue attachment member 106 remains attached to the inner wall 118 of the gastrointestinal tract until the tissue attachment member 106, the capsule 102, and/or other elements of the swallowable drug delivery device 100 are broken down and/or absorbed by the gastrointestinal tract. In the activated state, the tissue attachment member 106 may inhibit or prevent movement of the capsule 102 relative to the wall 118 of the gastrointestinal tract via friction, adhesion, physical abutment, or some combination thereof. While the tissue attachment member 106 in FIGS. 1A and 1B is single structure, in other embodiments the tissue attachment member 106 may be comprised of multiple distinct or interconnected structures.

The tissue attachment member 106 may be configured to change from the initial state to the activated state in response to an in vivo condition (e.g., in vivo stimuli) associated with the gastrointestinal tract at the predetermined location. The in vivo condition may be, for example, any one or combination of a predetermined temperature, pH, enzyme, and electrical conductivity in the gastrointestinal tract. In some embodiments the tissue attachment member 106 may passively sense the in vivo condition and in response change from the initial state to the activated state. In certain such embodiments, the tissue attachment member 106 may be made of a shape memory material such as, for example, a shape memory alloy and/or a shape memory polymer (e.g., a biodegradable shape memory polymer). Certain such shape memory materials may be deformed (e.g., compressed) at a first temperature and return to a pre-deformed shape when exposed to a second temperature that is higher than the first temperature. Other such shape memory materials, such as a pH-sensitive shape memory polymer, may change shape (e.g., expand or contract) in response to an increase or decrease of pH of a surrounding environment. In some embodiments, a pH-sensitive shape memory polymer used to construct the tissue attachment member 106 may cause the tissue attachment member 106 to change from the initial state to the activated state in response to a pH greater than or equal to approximately (e.g., ±10%) three (3), or a pH greater than or equal to approximately (e.g., ±10%) four (4), or a pH greater than or equal to approximately (e.g., ±10%) five (5). In some embodiments, the shape memory material may change shape in response to exposure to particular enzyme(s) or a concentration of enzyme(s) existing in the gastrointestinal tract including at the predetermination location in the gastrointestinal tract. In some embodiments, it may be any combination of temperature, pH, and enzyme(s) that cause the shape memory material used to construct the tissue attachment member 106 to change shape.

In some embodiments, electronic sensor(s), including, for example, optical and/or ultrasonic sensor(s), may be incorporated into the swallowable drug delivery device 100 for detecting the in vivo condition. In some embodiments, the electronic sensor(s) may output a signal to a local and/or remote controller, which, in turn, may analyze the signal and based on that analysis output a control signal causing the tissue attachment member 106 to change from the initial state to the activated state.

In some embodiments, a shape and/or orientation of the tissue attachment member 106 may change when the tissue attachment member 106 changes from the initial state to the activated state. For example, as seen in the transition from FIG. 1A to FIG. 1B, the tissue attachment member 106 changes from an orientation where it is parallel to a longitudinal axis A of the capsule 102 to an orientation where it is angled (i.e., non-parallel) to the longitudinal axis A of the capsule 102. The change in the shape and/or orientation of the tissue attachment member 106 may increase an outer dimension (e.g., an outer diameter or an outer width) of the swallowable drug delivery device 100 such that swallowable drug delivery device 100 engages (e.g., frictionally engages) the inner wall 118 of the gastrointestinal track in such a way that further movement of the swallowable drug delivery device 100 relative to the inner wall 118 of the gastrointestinal track is prevented or substantially inhibited. In the embodiment in FIGS. 1A and 1B, the outer dimension of the swallowable drug delivery device 100 that is increased is an outer width of the swallowable drug delivery device 100 measured perpendicular to the longitudinal axis A of the capsule 102. In some embodiments, at least a portion of the swallowable drug delivery device 100 has a cross section that is perpendicular or otherwise non-parallel to the longitudinal axis A of the capsule, and an area of that cross section may increase when the tissue attachment member 106 changes from the initial state to the activated state.

In addition, or as an alternative, to a change in the shape and/or orientation of the tissue attachment member 106, the tissue attachment member 106 may move in a radial direction away from the longitudinal axis A of the capsule 102 when the tissue attachment member 106 changes from the initial state to the activated state in some embodiments. Alternatively, in some embodiments, the tissue attachment member 106 may not undergo a change in shape, orientation, radial position, etc. in changing from the initial state to the activated state and as such there is no change in an outer dimension of the swallowable drug delivery device 100. Instead, the tissue attachment member 106 may be an adhesive (e.g., a mucoadhesive or other bioadhesive) which goes from being covered to uncovered as a result of the transition from the initial state to the activated state. In some embodiments, an adhesive which goes from being covered to uncovered, or which is always uncovered, may be used in conjunction with (e.g., applied to) a tissue attachment member which changes shape, orientation, and/or radial position when transitioning from the initial state to the activated state.

In some embodiments, the tissue attachment member 106 and the tissue delivery member 108 may be separate structures; whereas, in other embodiments, the tissue attachment member 106 and the tissue delivery member 108 may be the same structure.

In the initial state, the tissue attachment member 106 may be disposed on the exterior surface of the wall 114 of the capsule 102, or alternatively, may be disposed partially or entirely within the interior space of the capsule 102. In some embodiments, a groove or recess may be formed in the exterior surface of the wall 114 of the capsule 102 and the tissue attachment member 106 may be received in this groove or recess. In certain such embodiments, in the initial state, an exterior surface of the tissue attachment member 106 may be flush with and/or match the contour of the exterior surface of the wall 114 of the capsule 102, in order to provide a smooth surface facilitating passage (e.g., sliding) of the swallowable drug delivery device 100 through the gastrointestinal tract until it reaches the predetermined location for attachment and drug delivery.

As described in more detail below with respect to various embodiments, the tissue attachment member 106 may be formed by one or more expandable members (e.g., one or more expandable anchors). The expandable member(s) may in certain embodiments be solid (i.e., not hollow) whereas in other embodiments the expandable member(s) may be hollow. In some embodiments, the expandable member(s) may be configured as one or more bladders each being made of a flexible material and capable of being filled with a gas (e.g., air) and/or fluid (e.g., a drug) which causes the bladder to expand.

The coating 112 may cover a limited portion of the exterior surface of the wall 114 of the capsule 102 as shown in FIG. 1A, or, alternatively, may cover the entirety of the exterior surface of the capsule 102 so as to effectively form a shell encapsulating the capsule 102. Initially, the coating 112 may cover one or both of the tissue attachment member 106 and the tissue penetrating delivery member 108. The coating 112 may be made of a material that degrades (e.g., dissolves, breaks apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 100 is swallowed by the patient) and/or exposure to enzyme(s), a concentration of enzyme(s), and/or a pH unique to a particular portion of the gastrointestinal tract such as the small intestine. In some embodiments, the coating 112 may be a pH-sensitive coating that does not dissolve until exposure to the higher pH environment of the small intestine. In some embodiments, the coating 112 may be an enteric coating including, for example, a polymer based enteric coating.

FIG. 1B illustrates the swallowable drug delivery device 100 after the coating 112 has dissolved. With the coating 112 dissolved, the tissue attachment member 106 and the tissue penetrating delivery member 108 may be uncovered. Simultaneous with, as a consequence of, or subsequent to dissolution of the coating 112, the tissue attachment member 106 may change from the initial state to the activated state. Once the coating 112 has dissolved, the first end of the tissue penetrating delivery member 108 may be permitted to penetrate into the inner wall 118 of the gastrointestinal tract to deliver the drug. In other embodiments, the coating 112 may cover the tissue penetrating delivery member 108 but not the tissue attachment member 106, or vice versa.

The actuator 110 may be disposed partially or entirely within the interior space of the capsule 102. The actuator 110 may be configured to move the drug out of the reservoir 104 and into the gastrointestinal tract, including, for example, into the wall 118 of the gastrointestinal tract. Additionally or alternatively, the actuator 110 may be configured to move the tissue attachment member 106 from the initial state to the activated state. In some embodiments, the actuator 110 may include but is not limited to: an electromechanical drive mechanism such as, for example: a piezoelectric pump; a MEMS pump; a sonophoresis drive mechanism; a positive displacement pump; a spring such as, for example, a spring made of a shape memory polymer and/or a shape memory alloy; an inflatable bladder; and/or an osmotic pump. In some embodiments, the actuator 110 may push on a piston (e.g., a plunger) which, in turn, moves through the reservoir 104 to expel the drug from the reservoir 104.

In some embodiments, the actuator 110 may be omitted and the drug may be pushed out of the reservoir 104 into the gastrointestinal tract and as a result of natural movements (e.g., peristaltic movements) of the gastrointestinal tract. In some embodiments where the actuator 110 is omitted, an external (e.g., ex vivo) device may provide the energy needed for moving the drug out of the reservoir 104. In such embodiments, the external device may include a magnet, an electromagnet, an inductor, and/or a radiofrequency (RF) energy source for generating the needed to move the drug out of the reservoir 104.

In use, a patient may place the swallowable drug delivery device 100 in his or her mouth and swallow the swallowable drug delivery device 100. The swallowable drug delivery device 100 may then be pushed by, for example, natural movements (e.g., peristaltic movements) of the wall of the gastrointestinal tract, through the gastrointestinal tract toward a predetermined location (e.g., a region, an area, or a specific position) where attachment and drug delivery is to occur. In some embodiments, the predetermined location may correspond to a location where the thickness of the wall 118 of the gastrointestinal tract is at or near its thinnest. In some embodiments, the predetermined location is in the small intestine, although the predetermined location is not limited to the small intestine and may be anywhere along the gastrointestinal tract where optimal conditions for drug delivery exist. Gradually on the journey towards and/or at the predetermined location the coating 112 may dissolve or otherwise degrade to uncover the tissue attachment member 106 and the tissue penetrating delivery member 108. Simultaneous with the coating 112 degrading or subsequent to the coating 112 degrading, the tissue attachment member 106 may change from the initial state (FIG. 1A) to the activated state (FIG. 1B). In the present embodiment, this change corresponds to the tissue attachment member 106 rotating outwardly away from the wall 114 of the capsule 102 and frictionally engaging and/or penetrating the inner wall 118 of the gastrointestinal tract. As a consequence, the swallowable drug delivery device 100 is immobilized or substantially inhibited from further movement relative to the inner wall 118 of the gastrointestinal tract. In the present embodiment, the tissue attachment member 106 in addition to immobilizing the capsule 102 creates a pivot point allowing an end of the capsule 102 from which the tissue penetrating delivery member 108 protrudes to rotate towards the inner wall 118 of the gastrointestinal tract, as seen in FIG. 1B. This, in turn, causes the first or pointed end of the tissue penetrating delivery member 108 to penetrate into the inner wall 118 of the gastrointestinal tract. Thereafter, the actuator 110 may be activated to move the drug out of the reservoir 104, then through the interior passage of the tissue penetrating delivery member 108, then out of the tissue penetrating delivery member 108 via the one or more openings in the first or pointed end, and then directly into the inner wall 118 of the gastrointestinal tract.

Turning to FIGS. 2-12, various embodiments of a swallowable drug delivery device will now be described. Various elements of the swallowable drug delivery devices illustrated in FIGS. 2-12 may be similar in function and/or structure to elements of the drug delivery device 100 described above in conjunction with FIGS. 1A and 1B. Such elements are assigned with the same reference numeral as used in FIGS. 1A and 1B, except incremented by 100 or a multiple thereof. A description of some of these elements is abbreviated or eliminated in the interest of conciseness. Details of the structure and/or function that differentiate the embodiments illustrated in FIGS. 2-12 from the embodiment in FIGS. 1A and 1B are the focus of the discussion below.

Some embodiments of the swallowable drug delivery device may utilize a tissue attachment member that includes one or more expandable members (e.g., expandable anchors). The one or more expandable members may in the initial state have a non-expanded form or shape and in the activated state have an expanded form or shape. In some embodiments, after drug delivery is complete, the one or more expandable members may degrade (e.g., dissolves, breaks apart into smaller pieces, etc.) from exposure to enzyme(s) and/or other degrading element(s) in the gastrointestinal tract, including, for example, after exposure to such element(s) for a predetermined amount of time (for example, 8-12 hours after the swallowable drug delivery device is swallowed by the patient) and/or exposure to enzyme(s), a concentration of enzyme(s), and/or a pH unique to a particular portion of the gastrointestinal tract such as the small intestine. As an alternative to or in addition to degrading after drug delivery, the one or more expandable members may retract or return to their non-expanded form or shape. After the one or more expandable members have degraded and/or returned to their non-expanded form or shape, the capsule may detach from the inner wall 118 of the gastrointestinal tract and as a consequence continue its natural passage through the gastrointestinal tract and/or degrade (e.g., dissolve, breaks apart into smaller piece, etc.) and thereafter be absorbed by the gastrointestinal tract or expelled via the anus.

Figures 2A, 2B, 2C, 3A, 3B, 3C:
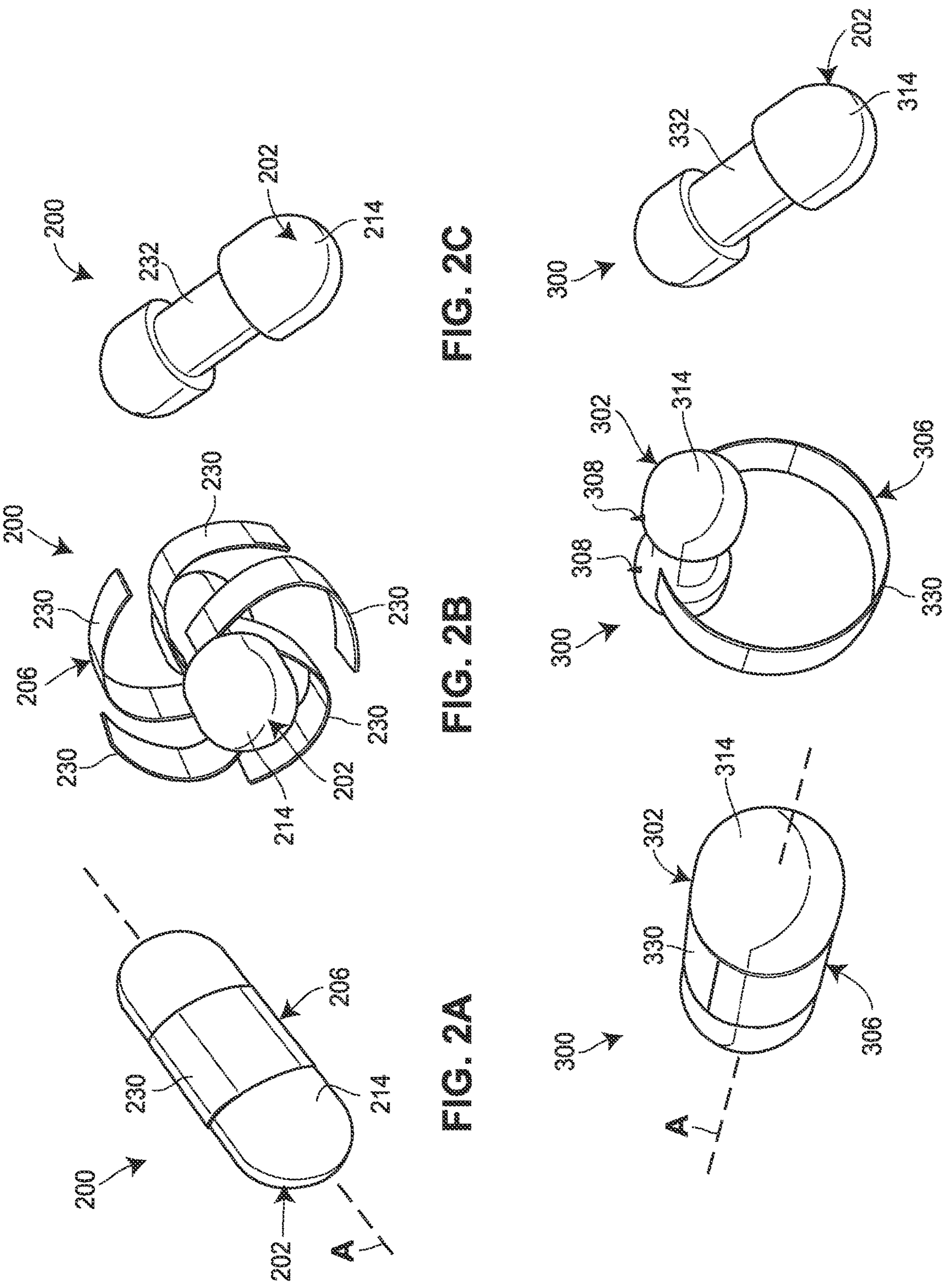
FIG. 2A is a perspective view of a swallowable drug delivery device according to another embodiment of the present disclosure, with a tissue attachment member in an initial state.
FIG. 2B is a perspective view of the swallowable drug delivery device in FIG. 2A, with the tissue attachment member in an activated state.
FIG. 2C is a perspective view of the swallowable drug delivery device in FIG. 2B after drug delivery has been completed.
FIG. 3A is a perspective view of a swallowable drug delivery device according to another embodiment of the present disclosure, with a tissue attachment member in an initial state.
FIG. 3B is a perspective view of the swallowable drug delivery device in FIG. 3A, with the tissue attachment member in an activated state.
FIG. 3C is a perspective view of the swallowable drug delivery device in FIG. 3B after drug delivery has been completed.

FIGS. 2A-2C illustrate an embodiment of a swallowable drug delivery device 200 having a tissue attachment member 206 corresponding to a plurality expandable members 230. In some embodiments, the expandable members 230 may be made of a shape memory polymer including, for example, a biodegradable shape memory polymer. In the illustrated embodiment, the expandable members 230 each is solid but in other embodiments they may each possess a hollow interior. The shape memory polymer used to construct the expandable members 230 may be sensitive to various stimuli including, for example, temperature, a pH of a surrounding environment, and/or enzyme(s).

In the initial state shown in FIG. 2A, the expandable members 230 each may have a circular or semi-circular shape centered about the longitudinal axis A of the capsule 202 and the expandable members 230 may be arranged adjacent to each other at distinct locations along the longitudinal axis A of the capsule 202. Also, in the initial state, each of the expandable members 230 may be received in a recess 230 formed in the exterior surface of the wall 214 of the capsule 202. As a consequence of this configuration, the exterior surface of the expandable members 230 may be flush with the exterior surface of the wall 214 of the capsule 202. This may provide the swallowable drug delivery device 200 with a smooth exterior that facilitates passage through the gastrointestinal tract (including, e.g., through the esophagus) prior to reaching the predetermined location for attachment and drug delivery.

In the activated state shown in FIG. 2B, each of the expandable members 230 has transformed into its expanded shape. As a consequence of this transformation, a diameter and/or radius of curvature of each of the expandable members 230 may increase. In the present embodiment, each expandable member 230 changes from having a circular shape to semi-circular shape (e.g., a letter "c" like shape). In alternative embodiments, each expandable member 230 may change from a circular shape to a non-circular shape when changing from the initial state to the activated state. A first end of each of the expandable members 230 may remain attached to the wall 214 of the capsule 202; and a second end of each of the expandable member 230 may move radially outwardly away from the longitudinal axis A. In addition, each expandable member 230 may rotate about its first end attached to the wall 214 of the capsule 202 in changing from the initial state to the activated state. In the activated state, the expandable members 230 may contact the inner wall 118 of the gastrointestinal tract in such a way so as to inhibit or prevent, via friction, physical abutment, or some combination thereof, movement of the capsule 202 relative to the wall 118 of the gastrointestinal tract. As a result, the capsule 202 may be immobilized at a predetermined location within the gastrointestinal tract where optimal conditions for drug delivery exist. In the present embodiment, the swallowable drug delivery device 202 releases or expels the drug into a lumen or interior space of the gastrointestinal tract, for example, via an opening in the wall 214 of the capsule 202.

In other embodiments, the swallowable drug delivery device 202 may be configured to deliver the drug directly into the wall 118 of the gastrointestinal tract, for example, via a tissue penetrating delivery member such as that described above in connection with FIGS. 1A and 1B.

In some embodiments, the expandable members 230 may be covered with a coating (e.g., the coating 112) in the initial state. The coating may restrain the expandable members 230 from expanding. As the swallowable drug delivery device 200 moves through the gastrointestinal tract, the coating may degrade, thereby allowing the expandable members 230 to change into the activated state. In certain such embodiments, the expandable members 230 each may be made of an elastic material that is held in a compressed state by the coating and, when the coating degrades, the elastic material returns to its uncompressed state, thereby resulting in expansion of the expandable member 230.

FIG. 2C illustrates the swallowable drug delivery device 200 after drug delivery is complete. In this state, the expandable members 230 have dissolved or broken away from the capsule 202 as a consequence of extended exposure to degrading elements of the gastrointestinal tract. The capsule 202 may then detach from the wall 118 of the gastrointestinal tract and continue its natural passage through the gastrointestinal tract and/or degrade (e.g., dissolve, breaks apart into smaller piece, etc.) and thereafter be absorbed by the gastrointestinal tract or expelled via the anus. In alternative embodiments, instead of dissolving subsequent to drug delivery, the expandable members 230 may retract or return to their non-expanded form or shape shown in FIG. 2A. In some embodiments, the retraction may be triggered by exposure to a certain enzyme(s), a change in temperature, a change in pH, and/or another in vivo condition.

FIGS. 3A-3C illustrate an embodiment of a swallowable drug delivery device 300 which has similarities in structure and/or function to the swallowable drug delivery device 200 in FIGS. 2A-2C. Details of the structure and/or function that differentiate the swallowable drug delivery device 300 in FIGS. 3A-3C from the swallowable drug delivery device 200 in FIGS. 2A-2C are discussed below.

The swallowable drug delivery device 300 has a single expandable member 330 which functions as the tissue attachment member 306. It has circular or substantially circular shape in both the initial state (FIG. 3A) and the activated state (FIG. 3B). In the initial state, the expandable member 330 may be centered about the longitudinal axis A of the capsule 302; whereas, in the activated state, the expandable member 330 may not be centered about the longitudinal axis A of the capsule 302. As shown in FIG. 3B, in the activated state, a first end of the expandable member 330 remains coupled to the wall 314 of the capsule 302 and a second end of the expandable member 330 moves away from the wall 314 of the capsule 302. In a scenario where the predetermined location for attachment and drug delivery is within the intestinal tract or another generally tubular portion of the gastrointestinal tract, the second end of the expandable member 330 in the activated state may come into contact with a side of the inner wall 118 of the gastrointestinal tract and push the capsule 302 towards an opposite side of the inner wall 118 of the gastrointestinal tract such that the capsule 302 is pressed against the opposite side of the inner wall 118 of the gastrointestinal tract. Tissue penetrating delivery members 308 may extend outwardly away from the portion of the capsule 302 that is pressed against the opposite side of the gastrointestinal tract. Thus, as a consequence of expansion of the expandable member 330, pointed ends of the tissue penetrating delivery members 308 may be inserted into the wall 118 of the gastrointestinal tract. Thereafter, the drug in the capsule 302 may be injected directly into the wall 118 of the gastrointestinal tract via the tissue penetrating delivery members 308. After drug delivery is complete, the expandable member 330 may degrade as shown in FIG. 3C, thereby allowing the capsule 302 to detach from the wall 118 of the gastrointestinal tract and continue its passage through the gastrointestinal tract. In some embodiments, the tissue penetrating delivery member 308 may also degrade and/or retract into the interior space of the capsule 302 after drug delivery is complete.

In order to achieve the insertion functionality described above, the tissue penetrating delivery members 308 may, in some embodiments, be disposed on the same side of the capsule 302 as the first end of the expandable member 330, as seen in FIG. 3B. In such embodiments, the pointed ends of the tissue penetrating delivery members 308 may point in a direction that is opposite to a direction in which the second end of the expandable member 330 moves away from the capsule 302 when the expandable member 330 changes from the initial state to the activated state. In some embodiments, the tissue penetrating delivery members 308 may be configured as one or more microneedles, one or more needles, one or more nozzles, or any combination thereof.

FIGS. 4A-4D illustrate an embodiment of a swallowable drug delivery device 400 which has similarities in structure and/or function to the swallowable drug delivery device 300. Details of the structure and/or function that differentiate the swallowable drug delivery device 400 in FIGS. 4A-4D from the swallowable drug delivery device 300 in FIGS. 3A-3C are discussed below.

Figure 4A:
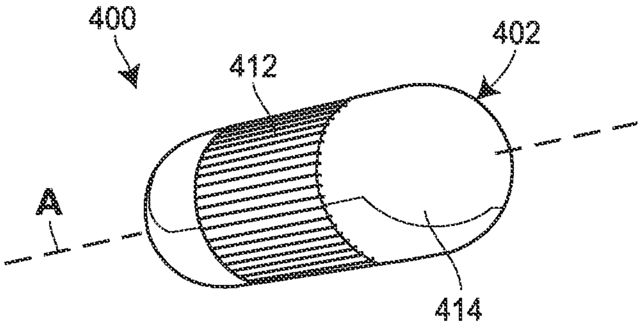
FIG. 4A is a perspective view of a swallowable drug delivery device according to another embodiment of the present disclosure, with a tissue attachment member in an initial state and covered by a coating.
Figure 4B:
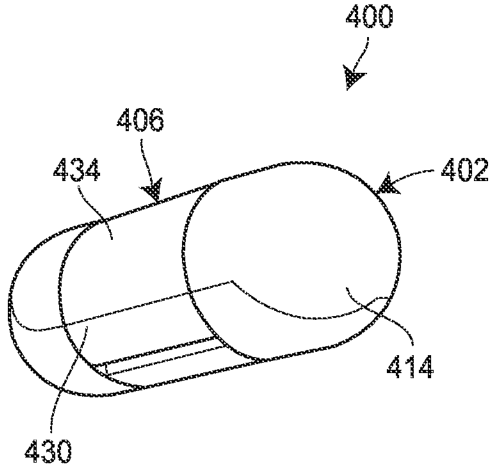
FIG. 4B is a perspective view of the swallowable drug delivery device in FIG. 4A, after the coating has dissolved.
Figure 4C:
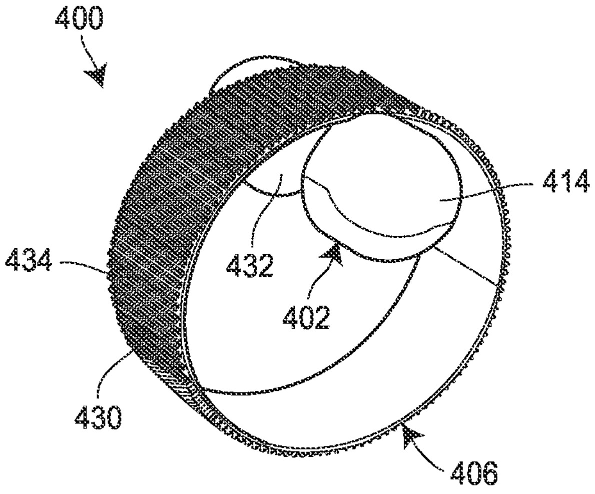
FIG. 4C is a perspective view of the swallowable drug delivery device in FIG. 4B, with the tissue attachment member in an activated state.
Figure 4D:
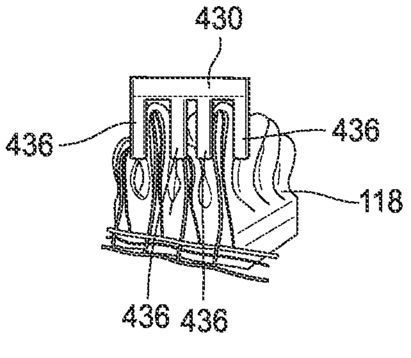
FIG. 4D is an enlarged view of a portion of the tissue attachment member in FIG. 4C interfacing with an inner wall of the gastrointestinal tract.

The swallowable drug delivery device 400 includes an expandable member 430 having an outer surface 434, which may be a radially outwardly facing surface, configured to meshingly engage with the wall 118 of the gastrointestinal tract in order to immobilize or substantially impede the swallowable drug delivery device 400 from further movement relative to the wall 118 of the gastrointestinal tract. FIG. 4A shows that in the initial state the outer surface 434 may be covered with the coating 412 so that the outer surface 434 does not meshingly engage with the wall 118 of the gastrointestinal tract. The coating 412 may degrade (e.g., dissolve, break apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 400 is swallowed by the patient) and/or exposure to enzyme(s), a concentration of enzyme(s), and/or a pH unique to a particular portion of the gastrointestinal tract such as the small intestine. FIG. 4B illustrates the swallowable drug delivery device 400 after the coating 412 has degraded and as a result exposed the outer surface 434 of the expandable member 430. FIG. 4C shows the expandable member 430 in the activated state. As illustrated schematically in FIG. 4D, the outer surface 434 includes a plurality of radially outwardly extending protrusions 436 which meshingly engage in an interlocking and/or intermingling manner with complementary biological structures protruding from the wall 118 of the gastrointestinal tract. As an alternative or in addition to the radially outwardly extending protrusions 436, the outer surface 434 of the expandable member 430 may include a texture that facilitate meshing engagement with the wall 118 of the gastrointestinal tract. In some embodiments, the manner in which the outer surface 434 meshingly engages with the wall 118 of the gastrointestinal tract may be similar to Velcro.

Figure 5A:
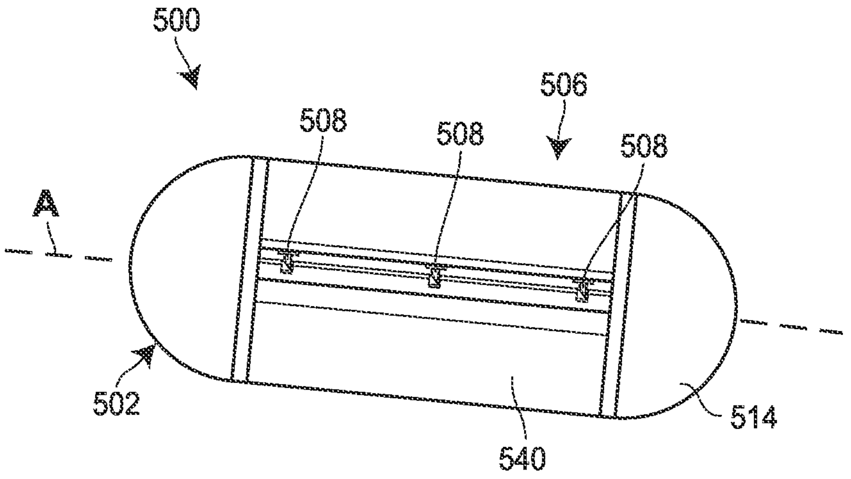
FIG. 5A is a perspective view of a swallowable drug delivery device according to another embodiment of the present disclosure, with a tissue attachment member in an initial state.
Figure 5B:
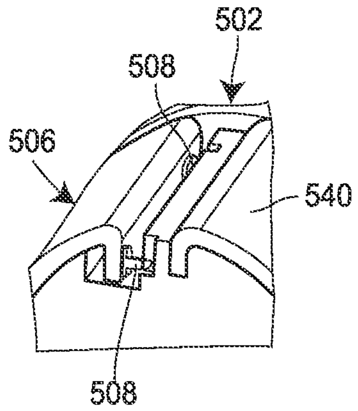
FIG. 5B is an enlarged cross-sectional view of a portion of a second end of the tissue attachment member illustrated in FIG. 5A.
Figure 5C:
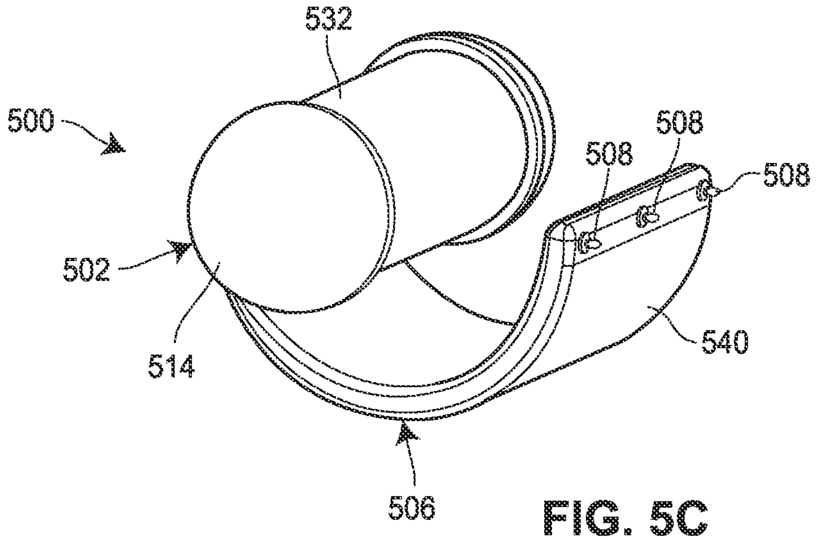
FIG. 5C is a perspective view of the swallowable drug delivery device in FIG. 5A, with the tissue attachment member in an activated state.

FIGS. 5A-5C illustrate an embodiment of a swallowable drug delivery device 500 which has similarities in structure and/or function to the swallowable drug delivery device 300 in FIGS. 3A-3C. Details of the structure and/or function that differentiate the swallowable drug delivery device 500 in FIGS. 5A-5C from the swallowable drug delivery device 300 in FIGS. 3A-3C are discussed below.

The swallowable drug delivery device 500 includes an expandable member 530 configured as an inflatable bladder 540. The inflatable bladder 540 may have an interior space that is empty or only partially filled with a gas (e.g., air) and/or fluid (e.g., a drug) in the initial state (FIGS. 5A and 5B) and filled with a gas (e.g., air) and/or fluid (e.g., a drug) to inflate the inflatable bladder in the activated state (FIG. 5C). In the activated state, a first end of the inflatable bladder 540 may remain coupled to the wall 514 of the capsule 502; whereas, a second end of the inflatable bladder 540 may rotate and move radially away from the capsule 502 such that the inflatable bladder 540 changes from having a substantially circular shape to a semi-circular (e.g., a letter "c" like shape). In some embodiments, the inflatable bladder 540 may be made of a flexible or elastic material including, for example, a thin polymer based film. In the present embodiment, the inflatable bladder 540 in the initial state wraps around the capsule 502 a single time; however, in other embodiments, the inflatable bladder 540 in the initial state may wrap around the capsule multiple times, including wrapping over itself multiple times. Increasing the number of times the inflatable bladder 540 wraps around the capsule 502 may result in a longer inflated length of the inflatable bladder 540 in the activated state. This may be beneficial depending on the predetermined location in the gastrointestinal tract where attachment and drug delivery is intended to occur.

Tissue penetrating delivery members 508 may be coupled to the second end of the inflatable bladder 540. In some embodiments, the tissue penetrating delivery members 508 may be configured as one or more microneedles, one or more needles, one or more nozzles, or any combination thereof. As shown in FIGS. 5A and 5B, in the initial state, the tissue penetrating delivery members 508 may be positioned in a recess formed in the wall 514 of the capsule 502 so that they are prevented or inhibited from coming into contact with the wall 118 of the gastrointestinal tract. To facilitate positioning of the tissue penetrating delivery members 508 in this recess, the second end of the expandable member 530 may be folded at least partially in the initial state, as seen in FIG. 5B. Upon inflation of the inflatable bladder 540 to achieve the activated state (FIG. 5C), second end of the expandable member 530 may unfold, thereby orienting the pointed ends of the tissue penetrating delivery members 508 to extend in a direction radially away from longitudinal axis A the capsule 502. As a result, the pointed ends of the tissue penetrating delivery members 508 may be oriented in such a way so as to facilitate penetration into the wall 118 of the gastrointestinal tract. Upon the completion of drug delivery, the inflatable bladder 540 may deflate and as a result the capsule 502 may detach from the wall 118 of the gastrointestinal tract and continue its natural passage through the gastrointestinal tract.

In some embodiments, a pressurized source of gas and/or fluid may be included in the capsule 502 for inflating the inflatable bladder 540 with gas and/or fluid at the appropriate time. In some embodiments, the pressurized source of gas and/or fluid may include a liquefied propellant that when released rapidly expands. In embodiments where the inflatable bladder 450 is inflated with a substance other than the drug, one of more fluid conduits (e.g., flexible tubing) may be disposed at least partially within the inflatable bladder 540 and may connect the tissue penetrating delivery members 508 in fluid communication with a drug reservoir in the capsule 502.

Figure 6A:
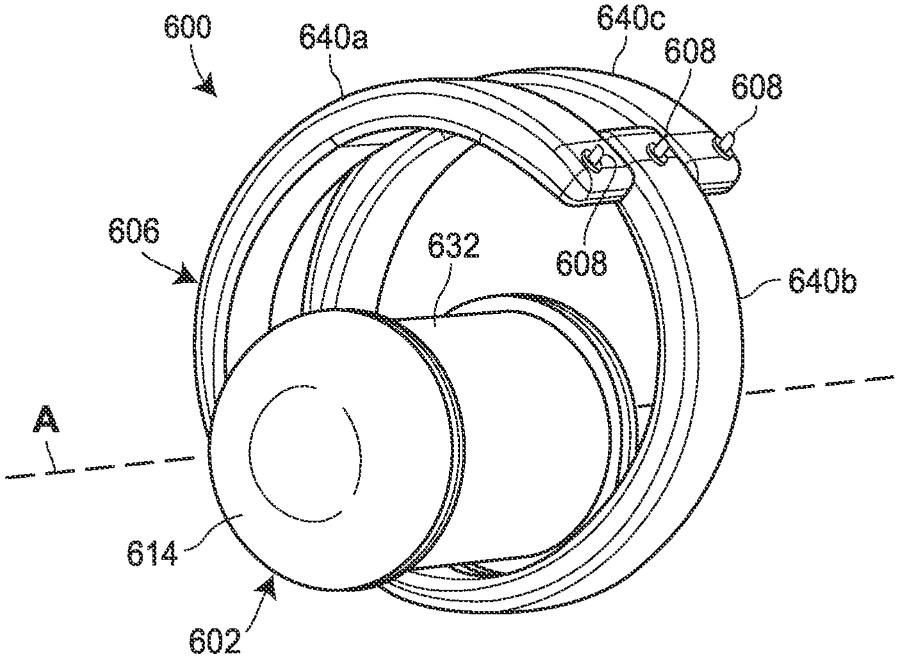
FIGS. 6A and 6B are perspective views of a swallowable drug delivery device according to another embodiment of the present disclosure.
Figure 6B:
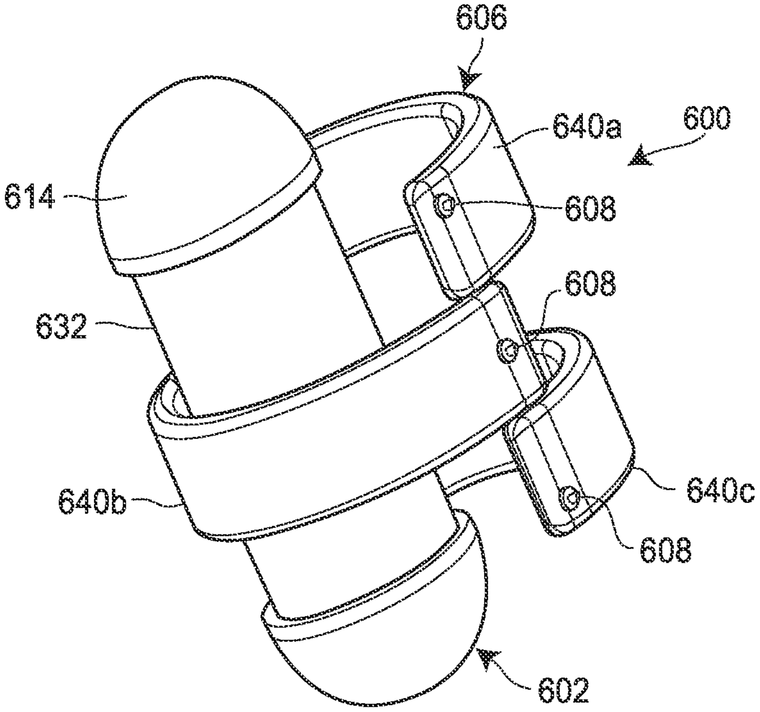

FIGS. 6A and 6B illustrate an embodiment of a swallowable drug delivery device 600 which has similarities in structure and/or function to the swallowable drug delivery device 500 in FIGS. 5A-5C. Details of the structure and/or function that differentiate the swallowable drug delivery device 600 in FIGS. 6A and 6B from the swallowable drug delivery device 500 in FIGS. 5A-5C are discussed below.

FIGS. 6A and 6B illustrate different perspective views of the swallowable drug delivery device 600 in the activated state. Multiple inflatable bladders 640*a*, 640*b*, and 640*c* have been inflated to secure the swallowable drug delivery device 600 to the wall 118 of the gastrointestinal tract. The inflatable bladders 640*a*, 640*b*, and 640*c* may be arranged at distinct axial positions along the longitudinal axis A of the capsule 602, as seen in FIGS. 6A and 6B. In the activated state, each of the inflatable bladders 640*a*, 640*b*, and 640*c* may have a semi-circular shape (e.g., a letter "c" like shape). Furthermore, in the activated state, the majority or the entirety of the inflatable bladder 640*b* may be arranged on one side of the capsule 602 and the majority or the entirety of each of the inflatable bladders 640*a* and 640*c* may be arranged on an opposite side of the capsule 602, as depicted in FIGS. 6A and 6B. Such an arrangement of the inflatable bladders 640*a*, 640*b*, and 640*c* may facilitate circumferential stability within a lumen of the gastrointestinal tract when the swallowable drug delivery device 600 is in the activated state.

The inflatable bladder(s) described above in connection with the swallowable drug delivery devices 500 and 600 are disposed outside of the capsule in the initial state. In other embodiments, such as the embodiment described below in conjunction with FIGS. 7A-7C, the inflatable bladder(s) may be disposed partially or entirely within the interior space of the capsule in the initial state and may be deployed outside of the capsule only in the activated state.

Figure 7A:
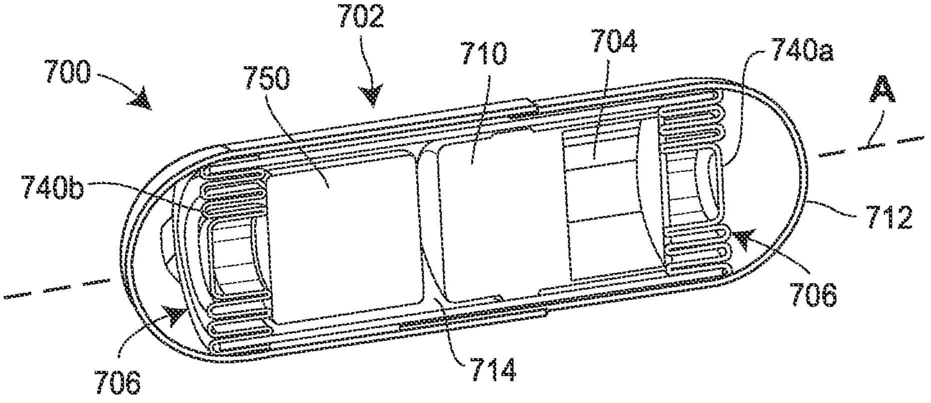
FIG. 7A is a cross-sectional view of a swallowable drug delivery device according to another embodiment of the present disclosure, with a tissue attachment member in an initial state.
Figure 7B:
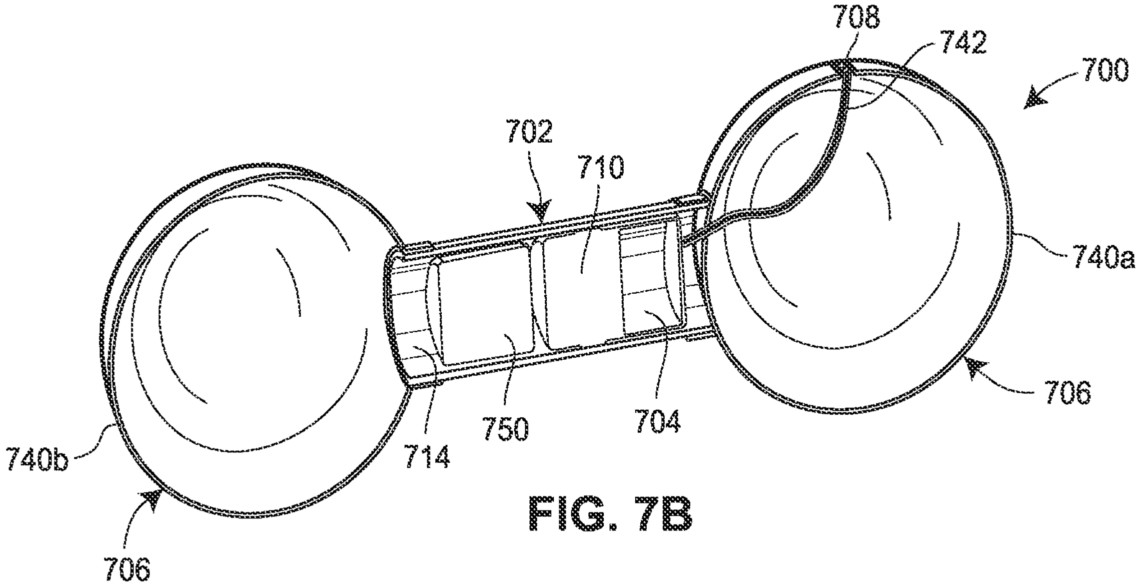
FIG. 7B is a cross-sectional view of the swallowable drug delivery device in FIG. 7A, with the tissue attachment member in an activated state.
Figure 7C:
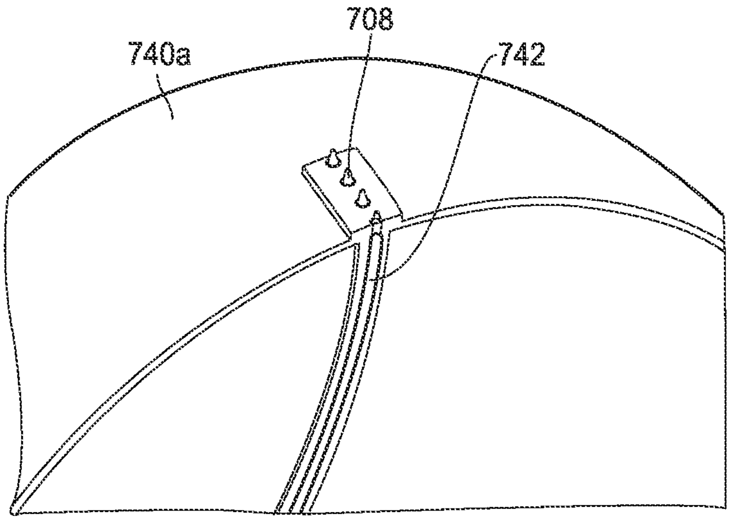
FIG. 7C is an enlarged cross-sectional view of a portion of the tissue attachment member illustrated in FIG. 7B.

FIGS. 7A-7C illustrate an embodiment of a swallowable drug delivery device 700 which has similarities in structure and/or function to the swallowable drug delivery device 500 in FIGS. 5A-5C. Details of the structure and/or function that differentiate the swallowable drug delivery device 700 in FIGS. 7A-7C from the swallowable drug delivery device 500 in FIGS. 5A-5C are discussed below.

FIG. 7A illustrates the inflatable bladders 740*a* and 740*b* in the initial state. Here, the inflatable bladders 740*a* and 740*b* are positioned within or mostly within the interior space of the capsule 702. Each of the inflatable bladders 740*a* and 740*b* may be folded one or more times or otherwise compressed so as to fit within the interior space of the capsule 702. A first opening and a second opening may be formed in opposite axial ends of the capsule 702. The inflatable bladder 740*a* may cover and seal close the first opening; and the inflatable bladder 740*b* may cover and seal close the second opening.

A pressurized source of gas and/or fluid 750 (e.g., a pressurized canister or cylinder) may be positioned within the interior space of the capsule 702 and may be configured for inflating the inflatable bladders 740*a* and 740*b* with gas and/or fluid. In some embodiments, the pressurized source of gas and/or fluid 750 may include a liquefied propellant that when released rapidly expands. In some embodiments, the gas and/or fluid released from the pressurized source of gas and/or fluid 750 may, in addition to inflating the inflatable bladders 740*a* and 740*b*, assist with moving the drug out of the reservoir 704 for delivery into the patient. In the present embodiment, an actuator 710 which is separate from the gas and/or fluid 750 is included for moving the drug out of the reservoir 704 for delivery into the patient. In some embodiment, the actuator 710 may be configured as a piezoelectric pump and, in some embodiments, may be controllable via a wireless signal (e.g., a Bluetooth) signal from an ex vivo device.

As shown in FIG. 7A, the capsule 702 may initially be covered with a protective layer or coating 712. In the present embodiment, the protective layer or coating 712 encapsulates the capsule 702 and effectively forms a shell. In other embodiments, the protective layer or coating 712 may be limited to covering one or both of the first and second openings in opposite axial ends of the capsule 702. The protective layer or coating 712 may degrade (e.g., dissolve, break apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 700 is swallowed by the patient) and/or exposure to enzyme(s), a concentration of enzyme(s), and/or a pH unique to a particular portion of the gastrointestinal tract such as the small intestine. Upon degrading, the inflatable bladders 740*a* and 740*b* may be allowed to deploy outside of the capsule 702 for attachment to the wall 118 of the gastrointestinal tract to define the activated state.

FIG. 7B depicts the inflatable bladders 740*a* and 740*b* in the activated state. Each of the inflatable bladders 740*a* and 740*b* may have a substantially spherical shape in the activated state. In some embodiments, the inflatable bladders 740*a* and 740*b* in the activated state may extend entirely across a lumen of the gastrointestinal tract at the predetermined location for attachment and drug delivery (e.g., a lumen of the small intestine). In the activated state, a pointed end of the tissue penetrating delivery member 708 may extend outwardly from the inflatable bladder 740*b* and may be oriented in a direction that is perpendicular or substantially perpendicular to the longitudinal axis A of the capsule 702. This configuration may aid the pointed end of the tissue penetrating delivery member 708 in penetrating the inner wall 118 of the gastrointestinal tract. In some embodiments, the tissue penetrating delivery member 708 may be configured as one or more microneedles, one or more needles, one or more nozzles, or any combination thereof. A fluid conduit 742 (e.g., flexible tubing) may extend between and connect in fluid communication the tissue penetrating delivery member 708 and the reservoir 704 so that during drug delivery the drug may flow out of the reservoir 704, through the fluid conduit 742, through the tissue penetrating delivery member 708, and into the wall 118 of the gastrointestinal tract.

While the foregoing embodiments of the swallowable drug device include a tissue attachment member that expands or otherwise changes shape in transitioning from the initial state to the activated state, other embodiments may have a tissue attachment member whose shape is the same or substantially the same in both the initial state and the activated state. Such embodiments are discussed below in conjunction with FIGS. 8A-12B.

Figure 8A:
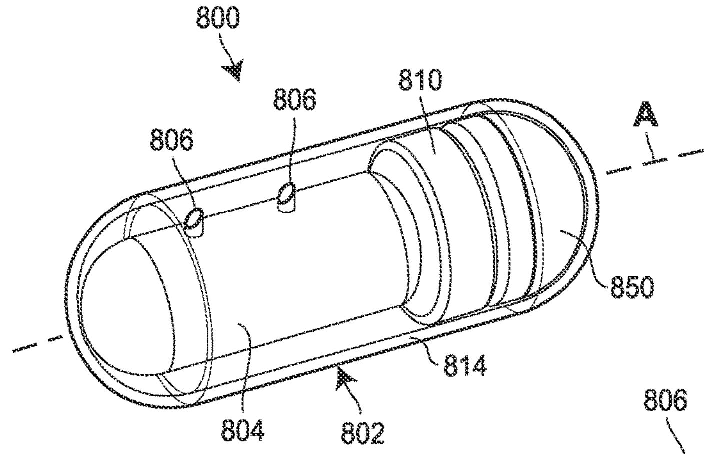
FIG. 8A is a perspective view of a swallowable drug delivery device according to another embodiment of the present disclosure, with a tissue attachment member in an initial state.
Figure 8B:
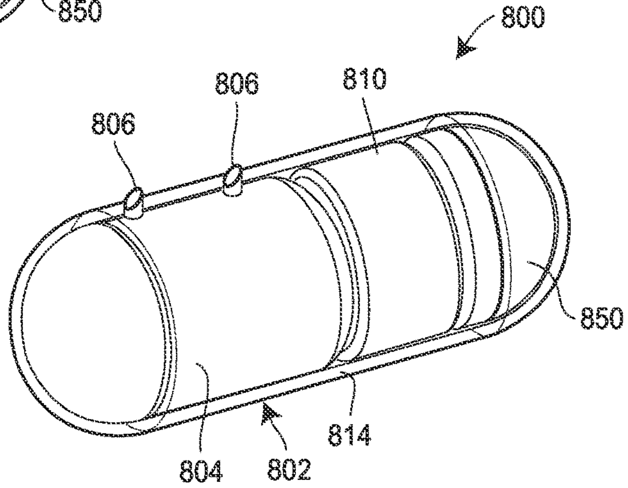
FIG. 8B is a perspective view of the swallowable drug delivery device in FIG. 8A, with the tissue attachment member in an activated state.

FIGS. 8A and 8B illustrate a swallowable drug delivery device 800 having tissue attachment members 806 which, in addition to securing the swallowable drug delivery device 800 to the wall 118 of the gastrointestinal tract in the activated state, are configured to deliver the drug into the wall 118 of the gastrointestinal tract. The tissue attachment members 806 are coupled to a wall (e.g., a circumferential wall) of the reservoir 804 and have pointed ends which extend outwardly from the wall of the reservoir 804. The tissue attachment members 806 may be configured as, for example, microneedles, needles, nozzles, or any combination thereof. The wall of the reservoir 804 may be made of a flexible (e.g., elastic) material such that the reservoir 804 is bladder like. In embodiments where the wall of the reservoir 804 is flexible, the reservoir 804 may be referred to as a drug storage bladder. In FIGS. 8A and 8B the wall 814 of the capsule 802 is illustrated as being semi-transparent; however, in reality the wall 814 of the capsule 802 may be opaque.

An actuator 810 is disposed within the capsule 802 adjacent to and in contact with the wall of the reservoir 804. As described below, the actuator 810 may be configured to expand and compress the reservoir 804 against an inner surface of the wall 814 of the capsule 802. In some embodiments, the actuator 810 may be an inflatable bladder which is inflated by a pressurized source of gas and/or fluid (e.g., a pressurized canister or cylinder). In some embodiments, the pressurized source of gas and/or fluid may include a liquefied propellant that when released expands rapidly. In other embodiments, the actuator 810 may be configured as a plurality of temperature-sensitive beads which expand in response to a change (e.g., increase or decrease) in temperature. In certain such embodiments, the beads may be made of a shape memory material (e.g., a shape memory polymer or a shape memory alloy).

In some embodiments, the swallowable drug delivery device 800 may include a sensing and communication module 850. The sensing and communication module 850 may be coupled (e.g., electrically coupled) with tissue attachment members 806 and may detect electrical continuity between the tissue attachment members 806 to confirm proper submucosa placement of the tissue attachment members 806.

FIG. 8A shows that in the initial state the pointed ends of the tissue attachment members 806 are disposed within the interior space of the capsule 802. When the capsule 802 has reached a predetermined location within the gastrointestinal tract, the actuator 810 may expand and push the reservoir 804 against an inner surface of the wall 814 of the capsule 802. This action may compress the reservoir 804 in the axial direction while simultaneously causing a circumferential portion of the wall of the reservoir 804 to move outwardly in the radial direction. As a result, the pointed ends of the tissue attachment members 806 may move through (e.g., penetrate through or protrude through holes in) the wall 814 of the capsule 802 and then penetrate into the wall 118 of the gastrointestinal tract to define the activated state (FIG. 8B). In some embodiments, the movement of the tissue attachment member s 806 may be in a radial direction away from the longitudinal axis A of the capsule 802. Further expansion of the actuator 810 may cause the interior fill volume of the reservoir 804 to decrease, thereby expelling the drug through the tissue attachment members 806 into the wall 118 of the gastrointestinal tract. After drug delivery is complete, in some embodiments the actuator 810 may detach from a remainder of the swallowable drug delivery device 800, which may allow the tissue attachment members 806 to retract inside the capsule 802 which, in turn, allows the capsule 802 to detach from the wall 118 of the gastrointestinal tract. In some embodiments, the actuator 810 may be configured to pull the tissue attachment members 806 back into the interior space of the capsule 802 so that the capsule 802 can detach from the wall 118 of the gastrointestinal tract after drug delivery is complete.

Figure 9A:
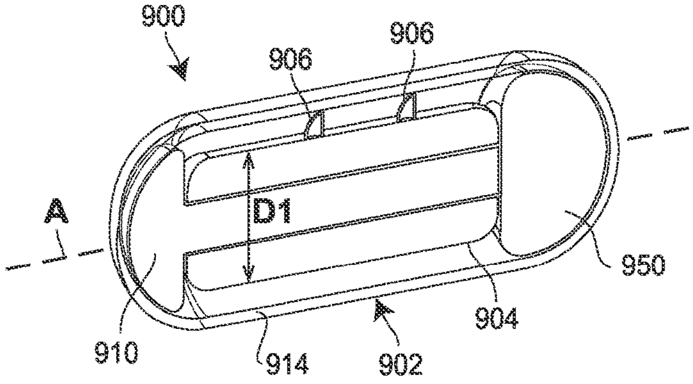
FIG. 9A is a cross-sectional view of a swallowable drug delivery device according to another embodiment of the present disclosure, with a tissue attachment member in an initial state.
Figure 9B:
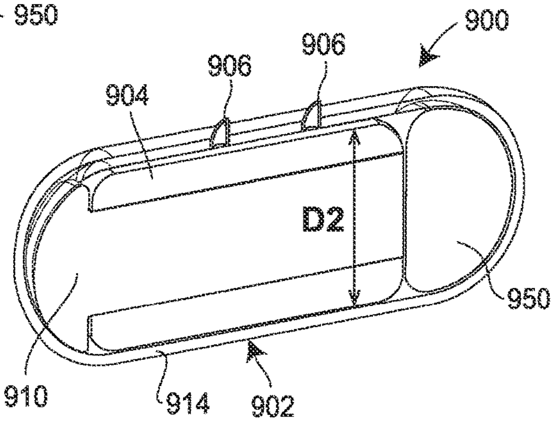
FIG. 9B is a cross-sectional view of the swallowable drug delivery device in FIG. 9A, with the tissue attachment member in an activated state.

FIGS. 9A and 9B illustrate an embodiment of a swallowable drug delivery device 900 which has similarities in structure and/or function to the swallowable drug delivery device 800 in FIGS. 8A and 8B. Details of the structure and/or function that differentiate the swallowable drug delivery device 900 in FIGS. 9A and 9B from the swallowable drug delivery device 800 in FIGS. 8A and 8B are discussed below. In FIGS. 9A and 9B the wall 914 of the capsule 902 is illustrated as being semi-transparent; however, in reality the wall 914 of the capsule 902 may be opaque.

FIG. 9A illustrates that the reservoir 904 has a hollow cylindrical or annular shape with an outer diameter D1 in the initial state. The reservoir 904 has a central passageway within which at least a portion of the actuator 910 is disposed. In some embodiments, the actuator 910 may be an inflatable bladder which is inflated by a pressurized source of gas and/or fluid (e.g., a pressurized canister or cylinder). Inflation of the inflatable bladder may push the reservoir 904 radially outwardly, causing the reservoir 904 to have an outer diameter D2 which is larger than the initial outer diameter D1. As a result, the pointed ends of the tissue attachment members 906 may move through (e.g., penetrate through or protrude through holes in) the wall 914 of the capsule 902 and subsequently penetrate into the wall 118 of the gastrointestinal tract to define the activated state (FIG. 9B). Further expansion of the actuator 910 may cause an interior fill volume of the reservoir 904 to decrease, thereby expelling the drug through the tissue attachment members 906 into the wall 118 of the gastrointestinal tract.

Figure 10A:
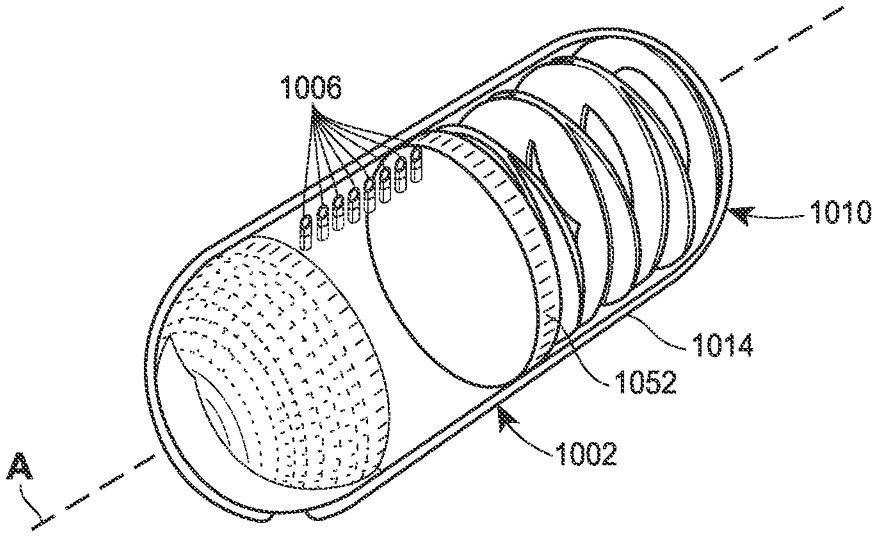
FIG. 10A is a perspective view of a swallowable drug delivery device according to another embodiment of the present disclosure, prior to drug delivery.
Figure 10B:
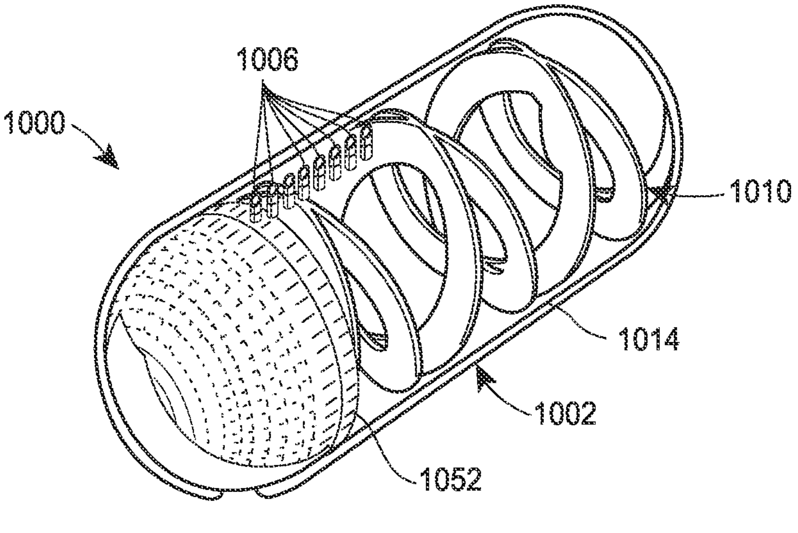
FIG. 10B is a perspective view of the swallowable drug delivery device in FIG. 10A, after drug delivery.

FIGS. 10A and 10B illustrate an embodiment of a swallowable drug delivery device 1000 which has similarities in structure and/or function to the swallowable drug delivery device 800 in FIGS. 8A and 8B. Details of the structure and/or function that differentiate the swallowable drug delivery device 1000 in FIGS. 10A and 10B from the swallowable drug delivery device 800 in FIGS. 8A and 8B are discussed below. In FIGS. 10A and 10B the wall 1014 of the capsule 1002 is illustrated as being semi-transparent; however, in reality the wall 1014 of the capsule 1002 may be opaque.

The swallowable drug delivery device 1000 includes an actuator 1010 disposed at least partially within the capsule 1002 and which is configured to expand to move the drug out of the reservoir 1004 into the wall 118 of the gastrointestinal tract. The reservoir 1004 may be defined at least by the wall 1014 of the capsule 1002 and a piston 1052 moveably disposed in the capsule 1002. Expansion of the actuator 1010 may cause the actuator 1010 to push on or otherwise act on the piston 1052 to move the piston 1052 relative to the wall 1014 to decrease a volume of the reservoir 1004, thereby expelling the drug from the reservoir 1004 into the wall 118 of the gastrointestinal tract. FIGS. 10A and 10B illustrates the position of the piston 1052, respectively, before and after drug delivery.

The actuator 1010 may be configured to expand, or contract depending on the configuration of the piston 1052, in response to an in vivo condition of the gastrointestinal tract at a predetermined location. To achieve this change in shape, the actuator 1010 may be constructed of a shape memory material such as, for example, a shape memory alloy and/or a shape memory polymer (e.g., a biodegradable shape memory polymer). Certain such shape memory materials may be deformed (e.g., compressed) at a first temperature and return to a pre-deformed shape when exposed to a second temperature that is higher than the first temperature. Other such shape memory materials, such as a pH-sensitive shape memory polymer, may change shape (e.g., expand or contract) in response to an increase or decrease in pH of a surrounding environment. In some embodiments, the shape memory material may change shape in response to exposure to particular enzyme(s) or concentration of enzyme(s) existing in the gastrointestinal tract including at a particular location in the gastrointestinal tract. In some embodiments, it may be any combination of temperature, pH, and enzyme(s) that cause the shape memory material used to construct the actuator 1010 to change shape. In some embodiments, opening(s) may be formed in the wall of the 1014 of the capsule 1002 to allow bodily fluids to flow into the interior space or compartment of the capsule 1002 where the actuator 1010 is disposed, such that the shape memory material used to construct the actuator 1010 is directly exposed to the temperature, pH, enzyme(s), or other in vivo condition intended to cause the shape memory material to change shape.

The actuator 1010 illustrated in FIGS. 10A and 10B has a double-helix configuration in order to provide a high output force when expanding. Other configurations are also possible including, for example, a single-helix configuration. The double-helix configuration of the present embodiment may be centered about the longitudinal axis A of the capsule 1002. During drug delivery, the double-helix configuration of the actuator 1010 may expand in length in a direction parallel to the longitudinal axis A of the capsule 1002. In some embodiments, expansion of the actuator 1010 may be similar in various respects to expansion of a coil spring.

The swallowable drug delivery device 1000 may have tissue attachment members 1006 which, in addition to securing the swallowable drug delivery device 1000 to the wall 118 of the gastrointestinal tract in the activated state, are configured to deliver the drug into the wall 118 of the gastrointestinal tract. The tissue attachment members 1006 are coupled to the wall 1014 (e.g., a circumferential wall) of the capsule 1002 and have pointed ends which extend outwardly from the wall 1014 of the capsule 1002. In some embodiments, the tissue attachment member 1106 may be fixedly coupled to the wall 1014 and thus may be immoveable relative to the wall 1014. A coating such as, for example, the coating 112 described above, may cover the pointed ends of the tissue attachment members 1006 in the initial state and subsequently degrade as a result of exposure to elements of the gastrointestinal tract to uncover the pointed ends of the tissue attachment members 1006 to enable the activated state at the predetermined location within the gastrointestinal tract.

Figure 11A:
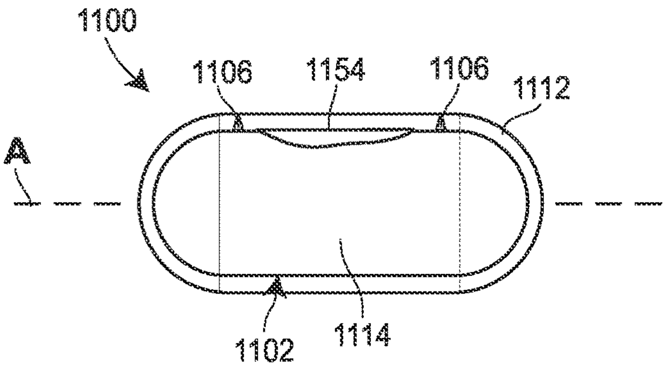
FIGS. 11A and 11B are perspective views of swallowable drug delivery device according to another embodiment of the present disclosure, with a tissue attachment member in an initial state.
Figure 11B:
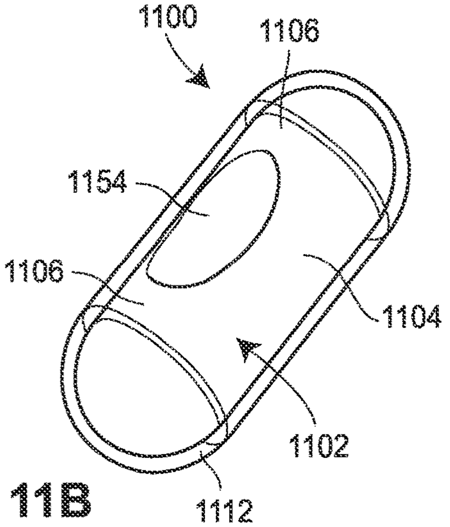

FIGS. 11A and 11B illustrate an embodiment of a swallowable drug delivery device 1100 which has similarities in structure and/or function to the swallowable drug delivery device 1000 in FIGS. 10A and 10B. Details of the structure and/or function that differentiate the swallowable drug delivery device 1100 in FIGS. 11A and 11B from the swallowable drug delivery device 1000 in FIGS. 10A and 10B are discussed below.

The swallowable drug delivery device 1100 includes a tissue attachment member 1106 comprised of an adhesive 1154. The adhesive 1154 may be applied to an exterior surface of the wall 1114 of the capsule 1102. In the initial state shown in FIGS. 11A and 11B, the adhesive 1154 may be covered by a coating 1112 so that the adhesive 1154 does not adhere to the wall 118 of the gastrointestinal tract. The coating 1112 may also cover the pointed ends of the tissue penetrating delivery members 1108 in the initial state, as seen in FIGS. 11A and 11B. The coating 1112 is depicted as being semi-transparent in FIGS. 11A and 11B but in reality may be opaque such that the adhesive 1154 and tissue penetrating delivery members 1108 are not visible in the initial state. The coating 1112 may degrade at and/or gradually during its passage through the gastrointestinal tract to the predetermined location for attachment and drug delivery. As a result, at the predetermined location the adhesive 1154 and the pointed ends of the tissue penetrating delivery members 1108 may be uncovered and may be able to at least selectively attach the capsule 1102 to the inner wall 118 of the gastrointestinal tract and deliver the drug into the inner wall 118 of the gastrointestinal tract. The tissue attachment members 1106 may be configured as, for example, microneedles, needles, nozzles, or any combination thereof.

In some embodiments, the adhesive 1154 may be a mucoadhesive including, for example, biocompatible adhesive polymer chains that intermingle with mucosa proteins to form a bond. The adhesive 1154 may be selected based on a particular gastrointestinal organ (e.g., the small intestine) where drug delivery is intended to occur.

The adhesive 1154 may be applied to a circumferential portion of the wall 1114 located on a first side of the capsule 1102, as shown in FIGS. 11A and 11B. The tissue penetrating delivery members 1108 may also be located on the first side of the capsule 1102, as seen in FIGS. 11A and 11B. As a result of this configuration, both the adhesive 1154 and tissue penetrating delivery members 1108 may come into contact with and secure to the wall 118 of the gastrointestinal tract.

The coating 1112 may be made of a material that degrades (e.g., dissolves, breaks apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 1100 is swallowed by the patient) and/or exposure to enzyme(s), a concentration of enzyme(s), and/or a pH unique to a particular portion of the gastrointestinal tract such as the small intestine. In some embodiments, the coating 1112 may be a pH-sensitive coating that does not dissolve until exposure to the higher pH environment of the small intestine. In some embodiments, the coating 1112 may be an enteric coating including, for example, a polymer based enteric coating.

In the embodiment illustrated in FIGS. 11A and 11B, the coating 1112 is applied to the entirety of the exterior surface of the wall 1114 and thus encapsulates the capsule 1102. In other embodiments, the coating 1112 may be omitted and instead the capsule 1102 may be encapsulated by a shell. This shell have the same degradable properties and/or function as the coating 1112 described above. In some embodiments, the coating 1112 may be applied to a limited portion of the capsule 1102, yet still covering at least the adhesive 1154 and/or the tissue penetrating delivery members 1108.

In the illustrated embodiment, the adhesive 1154 is applied to an exterior surface of the wall 1114 of the capsule 1102 in the initial state. In alternative embodiments, the adhesive 1154 may be disposed within the interior space of the capsule 1102 in the initial state. In such embodiments, the adhesive 1154 may be expelled through opening(s) in the wall 1114 of the capsule 1102 when the swallowable drug delivery device 1100 reaches the predetermined location. The coating 1112 may cover these opening(s) in the initial state and leave them uncovered in the activated state. The adhesive 1154 may be expelled from the interior of the capsule 1102 by a pump or other actuator included in the capsule 1102, thermal or chemical expansion, and/or natural peristaltic movement of the gastrointestinal tract. In some embodiments, the adhesive 1154 may be an expanding foam that partially or entirely fills a diameter of the intestinal tract and which dissolves after a short period of exposure to gastric fluids.

Figure 12A:
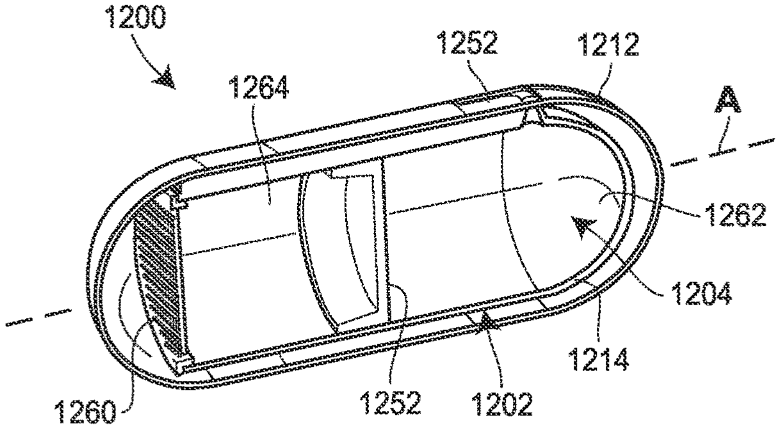
FIG. 12A is a cross-sectional view of a swallowable drug delivery device according to another embodiment of the present disclosure, with a tissue attachment member in an initial state.
Figure 12B:
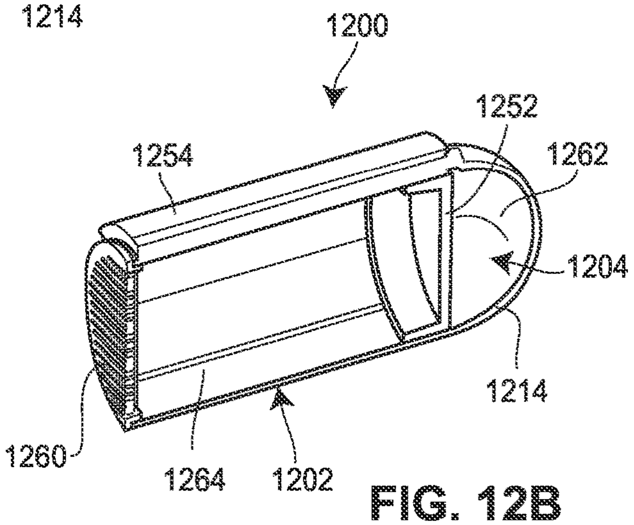
FIG. 12B is a cross-sectional view of the swallowable drug delivery device in FIG. 12A after drug delivery, with the tissue attachment member in an activated state.

FIGS. 12A and 12B illustrate an embodiment of a swallowable drug delivery device 1200 which has similarities in structure and/or function to the swallowable drug delivery device 1100 in FIGS. 11A and 11B. Details of the structure and/or function that differentiate the swallowable drug delivery device 1200 in FIGS. 12A and 12B from the swallowable drug delivery device 1100 in FIGS. 11A and 11B are discussed below.

FIGS. 12A and 12B illustrate the swallowable drug delivery device 1200 in, respectively, the initial state and the activated state. In the activated state, the coating 1212 has degraded to uncover the adhesive 1254 and a semipermeable membrane 1260. The semipermeable membrane 1260 may be coupled to and may cover an opening formed in the wall 1214 of the capsule 1202, for example, at an axial end of the capsule 1202. The capsule 1202 may include a piston 1252 (e.g., a plunger) that divides the interior space of the capsule 1202 into a first chamber 1262 and a second chamber 1264. The first chamber 1262 may correspond to the reservoir 1204 that is filled with the drug. The second chamber 1264 may be enclosed by at least the semipermeable membrane 1260, the wall 1214 of the capsule 1202, and the piston 1252. Furthermore, the second chamber 1264 may be filled with an osmotic material (e.g., an osmotic liquid). In the activated state where the exterior surface of the semipermeable membrane 1260 is uncovered, the semipermeable membrane 1260 may be configured to allow one or more bodily fluids to diffuse through the semipermeable membrane 1260 into the second chamber 1264, while simultaneously inhibiting or preventing fluid from flowing out of the second chamber 1264 through the semipermeable membrane 1260. As a consequence, the volume of fluid in the second chamber 1264 may increase, thereby pushing the piston 1252 in a direction causing it to decrease the interior fill volume of the first chamber 1262. The piston 1252, as a consequence, may push the drug out of the first chamber 1262 into the wall 118 of the gastrointestinal tract via one or more tissue penetrating delivery members (not illustrated). The one or more tissue penetrating delivery members may have pointed ends covered by the coating 1212 in the initial state and not covered by the coating 1212 in the activated state, as described above in relation to other embodiments of the present disclosure. The one or more tissue penetrating delivery members may be configured as, for example, microneedle(s), needle(s), nozzle(s), or any combination thereof. As an alternative or in addition to the one or more tissue penetrating delivery members, one or more openings may be formed in the wall 1214 of the capsule 1202 and the drug may expelled into the gastrointestinal tract via these opening(s).

The foregoing embodiments of the swallowable drug delivery device utilize self-deploying tissue attachment member(s) responsive to an in vivo condition in order to anchor the swallowable drug delivery device at the predetermined location in the gastrointestinal tract. In other embodiments, the swallowable drug delivery device may be used in conjunction with an ex vivo (e.g., outside of the patient's body) device in order to anchor the swallowable drug delivery device at the predetermined location in the gastrointestinal tract. An embodiment of a system including a swallowable drug delivery device and ex vivo device is described below in connection with FIG. 13.

Figure 13:
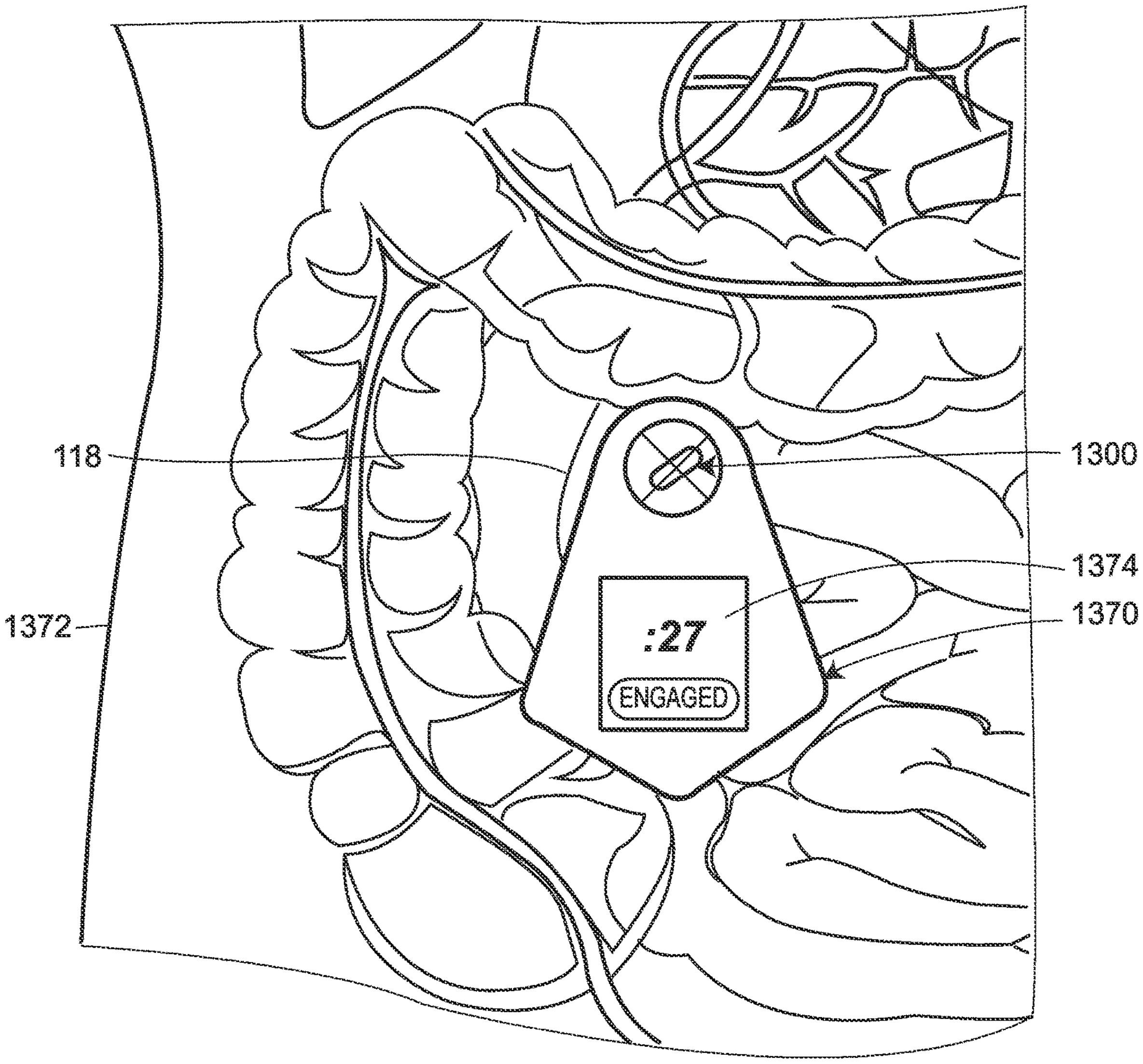
FIG. 13 is a schematic of a system including swallowable drug delivery device and an ex vivo control device according to another embodiment of the present disclosure.

FIG. 13 illustrates a system including a swallowable drug delivery device 1300 and an ex vivo device 1370. The ex vivo device 1370 may be positionable adjacent to a patient's abdomen 1372 and configured to immobilize the swallowable drug delivery device 1300 within the gastrointestinal tract and position the swallowable drug delivery device 1300 against the inner wall 118 of the gastrointestinal tract. The swallowable drug delivery device 1300 may be similar structure and function as any of the above-described embodiments of the swallowable drug delivery device 1300, except that the swallowable drug delivery device 1300 may not have a tissue attachment member that changes from an initial state to an activated state in response to an in vivo condition. However, some embodiments of the swallowable drug delivery device 1300 may incorporate a tissue attachment member of this kind, so long as the tissue attachment member supplements and/or does not interfere with the anchoring function of the ex vivo device 1370.

In some embodiments, the ex vivo device 1370 may be configured to magnetically interact (e.g., magnetically attract and/or magnetically repel) the swallowable drug delivery device 1300 in order to position (e.g., hold, immobilize, etc.) the swallowable drug delivery device 1300 against the inner wall 118 of the gastrointestinal tract at the predetermined (e.g., preselected, targeted, chosen, preferred, etc.) location for drug delivery. The swallowable drug delivery device 1300 may include a magnetic element that experiences a magnetic pull or push in the presence of a magnetic element included in the ex vivo device 1370. The magnetic element included in the swallowable drug delivery device 1300 may be any one or combination of: a permanent magnet, an electromagnet, a metallic element, a magnetic ceramic element, and any other magnetic-field generating element. The magnetic element included in the ex vivo device 1370 may be any one or combination of: a permanent magnet, an electromagnet, a metallic element, a magnetic ceramic element, and any other magnetic-field generating element.

The swallowable drug delivery device 1300 may include tissue penetrating delivery member(s) similar to those described above in connection with FIGS. 1A-12B. The tissue penetrating delivery member(s) may extend outwardly from an exterior surface of the swallowable drug delivery device 1300 so that when the swallowable drug delivery device 1300 is magnetically attracted or repelled by the ex vivo device 1370 the tissue penetrating delivery member(s) penetrate into the inner wall 118 of the gastrointestinal tract at the predetermined location for drug delivery. Subsequently, the drug may be released, expelled, etc. from the swallowable drug delivery device 1300 for delivery directly into the wall 118 of the gastrointestinal tract. In some embodiments, the tissue penetrating delivers member(s) may be configured to move from an initial position, where pointed end(s) of the tissue penetrating delivery member(s) are positioned within an interior space of the swallowable drug delivery device 1300 or otherwise are covered, to a delivery position, where the pointed ends(s) of the tissue penetrating delivery member(s) are positioned outside of the swallowable drug delivery device 1300 for penetrating into the inner wall 118 of the gastrointestinal tract. The tissue penetrating delivery member(s) may be configured as, for example, microneedle(s), needle(s), nozzle(s), or any combination thereof.

In some embodiments, the ex vivo device 1370 may be configured to wirelessly transmit power to (e.g., via inductive charging) the swallowable drug delivery device 1300 including, for example, when the swallowable drug delivery device 1300 is within the gastrointestinal tract. The swallowable drug delivery device 1300, in turn, may use this power to expel the drug from the swallowable drug delivery device and/or move the tissue penetrating delivery member(s) from the initial position to the delivery position. This may eliminate the need for including a pre-charged internal battery source within the swallowable drug delivery device 1300 and in some instances reduce the size of the swallowable drug delivery device 1300.

In some embodiments, the ex vivo device 1370 may be configured to transmit control signal(s) to the swallowable drug delivery device 1300 causing, for example, activation of an actuator included the swallowable drug delivery device 1300 for expelling the drug from the swallowable drug delivery device 1300, movement of the tissue penetrating delivery member(s) from the initial position to the delivery position, and/or the activation or execution of other functionalities of swallowable drug delivery device 1300.

As illustrated in FIG. 13, the ex vivo device 1370 may include an output unit 1374 configured for notifying the user (e.g., the patient or a caregiver) that the swallowable drug delivery device 1300 is proximate to (e.g., within a predetermined distance of) the ex vivo device 1370. This may assist the user with identifying where the swallowable drug delivery device 1300 is located within the gastrointestinal tract and determining whether the swallowable drug delivery device 1300 is located at the predetermined location for drug delivery. In some embodiments, the user may move the ex vivo device 1370 over the abdomen 1372 in order to search for the swallowable drug delivery device 1300. The output unit 1374 may additionally be configured to notify the user that the swallowable drug delivery device 1300 has begun and/or completed drug delivery. The output unit 1374 may include any one or combination of: a visual output unit (e.g., a display, a light, etc.), an audio output unit (e.g., a speaker), and a tactile output unit (e.g., a vibration generator).

In some embodiments, the ex vivo device 1370 may include a proximity sensor configured to determine whether the swallowable drug delivery device 1300 is within a predetermined distance of the ex vivo device 1370.

In the embodiment illustrated in FIG. 13, the ex vivo device 1370 may be held in the users hand(s) during use. In other embodiments, the ex vivo device 1370 may be temporarily secured to the patient's abdomen 1372 via, for example, a belt, strap, and/or skin adhesive.

Figure 14A:
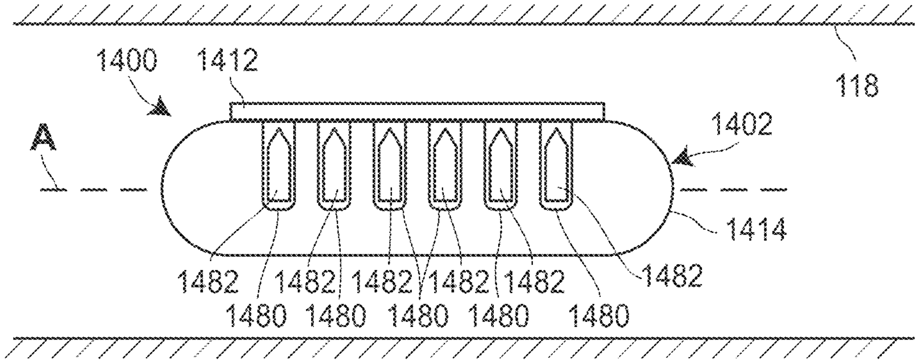
FIG. 14A is a schematic cross-sectional view of a swallowable drug delivery device according to another embodiment of the present disclosure, with drug-containing projectiles in an initial state.
Figure 14B:
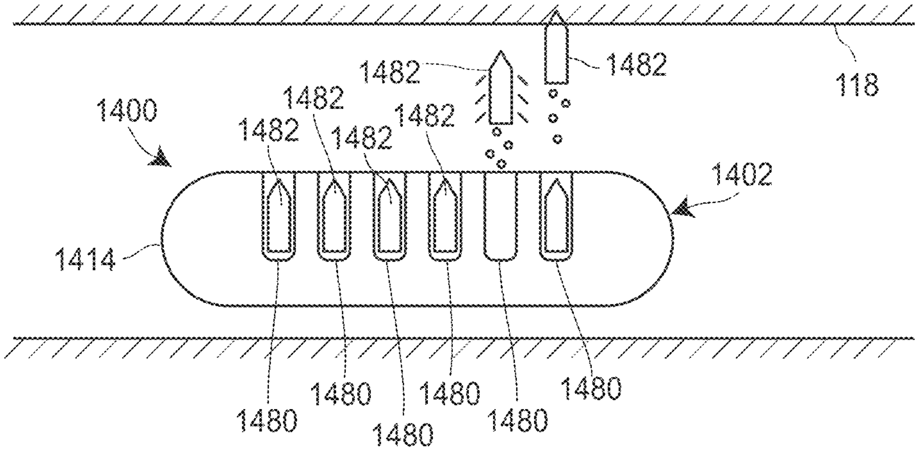
FIG. 14B is a schematic cross-sectional view of the swallowable drug delivery device in FIG. 14A, with some of the drug-containing projectiles in an activated state.

The foregoing embodiments of the swallowable drug delivery device generally operate to perform drug delivery by transferring a drug contained in a reservoir, which is coupled to a capsule, into the gastrointestinal tract. In other embodiments, the reservoir may physically separate from the capsule at the time of drug delivery. FIGS. 14A and 14B illustrate an embodiment of a swallowable drug delivery device 1400 configured to launch drug-containing projectiles into the inner wall 118 of the gastrointestinal tract. In some embodiments, these projectiles may be referred to as micro-rockets. The swallowable drug delivery device 1400 may have similarities in structure and/or function to one or more of the swallowable drug delivery devices described above in connection with FIGS. 1A-13. Details of the structure and/or function that differentiate the swallowable drug delivery device 1400 in FIGS. 14A and 14B from the above-described swallowable drug delivery devices are described below.

FIG. 14A illustrates that the capsule 1402 of the swallowable drug delivery device 1400 may include a plurality of launch bays 1480 and a respective one of a plurality of projectiles 1482 may be disposed in each of the launch bays 1480 in an initial state. In some embodiments, the launch bays 1480 may correspond to recesses, depressions, or slots formed in the wall 1414 of the capsule 1402. Each of the launch bays 1480 may have an opening that is covered in the initial state. In FIG. 14A, the opening of each of the launch bays 1480 is covered by a coating 1412. The coating 1412 may be made of a material that degrades (e.g., dissolves, breaks apart into smaller pieces, etc.) when exposed to enzyme(s) and/or other degrading element(s) in the gastrointestinal tract, including, for example, after exposure to such element(s) for a predetermined amount of time (for example, 8-12 hours after the swallowable drug delivery device 1400 is swallowed by the patient) and/or exposure to enzyme(s), a concentration of enzyme(s), and/or a pH unique to a particular portion of the gastrointestinal tract such as the small intestine. In some embodiments, the coating 1412 may be a pH-sensitive coating that does not dissolve until exposure to the higher pH environment of the small intestine. In some embodiments, the coating 1412 may be an enteric coating including, for example, a polymer based enteric coating.

Each of the projectiles 1482 may contain a drug and a propellant 1484, which may be stored in separate internal chambers walled off from each other. Each projectile 1482 may have first end and a second end. In some embodiments, the first end may be pointed to facilitate penetration into the wall 118 of the gastrointestinal tract. One or more openings may be formed in the first end of the projectile 1482 so that the drug can move out of the projectile 1482 when the projectile 1482 has penetrated into the wall 118 of the gastrointestinal tract. Additionally or alternatively, a wall of the projectile 1482 at the first end and/or the second end may be made of a material that degrades (e.g., dissolves, breaks apart into smaller pieces, etc.) when exposed to enzyme(s) and/or other degrading element(s) in the gastrointestinal tract, including, for example, after exposure to such element(s) for a predetermined amount of time. So configured, the drug contained in the projectile 1482 may be released into the wall 118 of the gastrointestinal tract at least partly as a result of degradation of the wall of the projectile 1482.

Figure 14C:
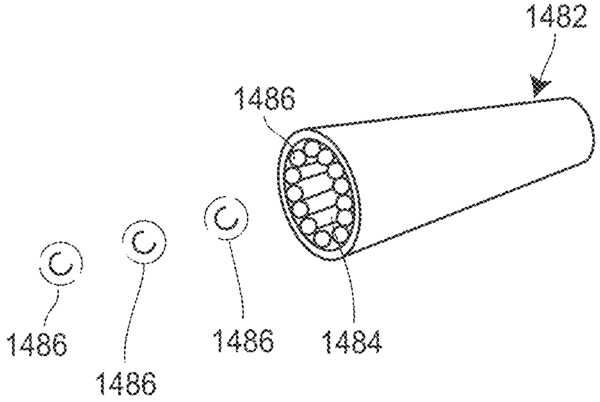
FIG. 14C is an enlarged perspective view of one of the drug-containing projectiles in FIG. 14B in the activated state.

The second end of each projectile 1482 may have an opening 1488 (FIG. 14C) that, when uncovered, allows bodily fluid(s) in the gastrointestinal tract to come into contact with the propellant 1484 inside of the projectile 1482. In some embodiments, the propellant 1484 in the projectile 1482 may undergo a chemical reaction when exposed to bodily fluid(s) (e.g., acidic gastric fluids) in the gastrointestinal tract. This chemical reaction may generate a gas 1486 (including, e.g., gas bubbles) which propels the projectile 1482 in a direction away from the capsule 1402 towards the wall 118 of the gastrointestinal tract at a predetermined location, as illustrated in FIG. 14B. In this sense, the projectiles 1482 may be considered to be self-propelled projectiles. In some embodiments, one or more of the projectiles 1482 may propel itself in a direction that is perpendicular or otherwise non-parallel to the longitudinal axis A of the capsule 1402.

In some embodiments, the propellant 1484 may be made, partially or entirely, of zinc and/or the gas 1486 generated in the activated state may be made, partially or entirely, of hydrogen. In some embodiments, the propellant 1484 may be made of PANI/Zn. In some embodiments, the chemical reaction that occurs when the propellant 1484 is exposed to an acidic environment in the gastrointestinal tract may be described by the following chemical formula: $2H^*(aq)+Zn(s) \rightarrow H_2(g)+Zn^{2+}(aq)$.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-$\alpha 4\beta 7$ mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF$\alpha$ monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-$\alpha$4integrin mAb); Valortim® (MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF$\alpha$ mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti- $\alpha 5\beta 1$ integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)-N-((S)-1-((S)-4-methyl-1-(R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™ or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12c small molecule inhibitor, or another product containing a KRASG12c small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A swallowable drug delivery device comprising:

a capsule containing a drug and sized to move through at least a portion of a gastrointestinal tract of a patient;

a tissue attachment member coupled to the capsule and having an initial state wherein the tissue attachment member allows the capsule to move through the at least a portion of the gastrointestinal tract and an activated state wherein the tissue attachment member is configured to at least selectively attach the capsule to a wall of the gastrointestinal tract;

the tissue attachment member being configured to change from the initial state to the activated state in response to an in vivo condition associated with the gastrointestinal tract at a predetermined location; and in the initial state:

the tissue attachment member being disposed on an exterior surface of the wall, and/or an exterior surface of the tissue attachment member being flush with and/or matching the contour of the exterior surface of the wall.

2. The swallowable drug delivery device of claim 1, wherein at least a portion of the tissue attachment member moves away from a longitudinal axis of the capsule when the tissue attachment member changes from the initial state to the activated state.

3. The swallowable drug delivery device of claim 1, wherein an outer dimension of the swallowable drug delivery device increases when the tissue attachment member changes from the initial state to the activated state.

4. The swallowable drug delivery device of claim 1, wherein at least a portion of the swallowable drug delivery device has a cross section perpendicular or non-parallel to a longitudinal axis of the capsule, wherein an area of the cross section of the swallowable drug delivery device increases when the tissue attachment member changes from the initial state to the activated state.

5. The swallowable drug delivery device of claim 1, wherein the tissue attachment member comprises one or more expandable members.

6. The swallowable drug delivery device of claim 1, comprising a coating applied to the tissue attachment member, wherein the coating degrades in response to exposure to the gastrointestinal tract to allow or cause the tissue attachment member to change from the initial state to the activated state.

7. The swallowable drug delivery device of claim 1, wherein the in vivo condition causing the tissue attachment member to change from the initial state to the activated state comprises at least one of a predetermined temperature, pH, enzyme, and electrical conductivity associated with the gastrointestinal tract at the predetermined location.

8. The swallowable drug delivery device of claim 1, comprising an actuator disposed at least partially within the capsule.

9. The swallowable drug delivery device of claim 1, comprising a tissue penetrating delivery member extending outwardly from the capsule and configured to deliver the drug from the capsule into the wall of the gastrointestinal tract.

10. A swallowable drug delivery device comprising:

a capsule containing a drug and sized to move through at least a portion of a gastrointestinal tract of a patient;

an adhesive disposed on an exterior surface of the capsule and configured to at least selectively attach the capsule to a wall of the gastrointestinal tract; and a coating or shell covering at least a portion of the adhesive and configured to degrade to uncover the at least a portion of the adhesive in response to an in vivo condition associated with the gastrointestinal tract at a predetermined location.

11. The swallowable drug delivery device of claim 10, wherein the in vivo condition comprises at least one of a predetermined temperature, pH, enzyme, and electrical conductivity associated with the gastrointestinal tract at the predetermined location.

12. The swallowable drug delivery device of claim 10, comprising a tissue penetrating delivery member extending outwardly from the exterior surface of the capsule and having an interior passage in fluid communication or configured to be connected in fluid communication with the drug in the capsule.

13. The swallowable drug delivery device of claim 12, wherein the coating or shell initially covers an opening formed in the at least one tissue penetrating delivery member.

14. The swallowable drug delivery device of claim 12, wherein the at least one tissue penetrating delivery member comprises one or more microneedles.

15. The swallowable drug delivery device of claim 10, wherein the adhesive comprises a mucoadhesive.

16. The swallowable drug delivery device of claim 10, comprising:

a piston moveably disposed within the capsule and dividing an interior of the capsule into a first chamber and a second chamber, wherein the drug is disposed in the first chamber;

an osmotic material disposed in the second chamber; and a semipermeable membrane coupled to the capsule such that the osmotic material is between an interior surface of the semipermeable membrane and the piston, wherein the coating or shell initially covers an exterior surface of the semipermeable membrane.

17. The swallowable drug delivery device of claim 16, wherein degradation of the coating or shell in response to the in vivo condition uncovers the exterior surface of the semipermeable membrane and allows at least one bodily fluid to diffuse through the semipermeable membrane into the second chamber, causing the piston to move the drug out of the first chamber for delivery to the gastrointestinal tract.

18. A system comprising:

a swallowable drug delivery device comprising:

a capsule containing a drug and sized to move through at least a portion of a gastrointestinal tract of a patient; and a tissue penetrating delivery member having an interior passage in fluid communication or configured to be connected in fluid communication with the drug; and an ex vivo device positionable adjacent to an abdomen of the patient and configured to magnetically interact with the swallowable drug delivery device to position the swallowable drug delivery device against a wall of the gastrointestinal tract, wherein the ex vivo device comprises a proximity sensor configured to detect proximity between the ex vivo device and the swallowable drug delivery device.

19. The system of claim 18, wherein the ex vivo device (a) comprises an electromagnet, (b) is configured to wirelessly transmit power to the swallowable drug delivery device, and/or (c) comprises an output device for notifying a user that the swallowable drug delivery device is proximate to the ex vivo device.

20. The system of claim 18, the tissue penetrating delivery member being configured to move from an initial position to a delivery position wherein the tissue penetrating delivery member is outside of the capsule for penetrating into the wall of the gastrointestinal tract.

21. The system of claim 20, the ex vivo device being configured to transmit a signal to the swallowable drug delivery device causing the tissue penetrating delivery member to move from the initial position to the delivery position.

22. The system of claim 18, wherein the tissue penetrating delivery member comprises one or more microneedles.

23. A swallowable drug delivery device comprising:

a capsule sized to move through at least a portion of a gastrointestinal tract of a patient; and a projectile containing a drug and having an initial state wherein the projectile is disposed at least partially within the capsule and an activated state wherein the projectile moves in a direction away from the capsule to separate from the capsule and penetrate into a wall of the gastrointestinal tract.

24. The swallowable drug delivery device of claim 23, wherein the projectile comprises a propellant for moving the projectile in the direction away from the capsule in the activated state.

25. The swallowable drug delivery device of claim 24, wherein the propellant undergoes a chemical reaction to generate a gas which propels the projectile in the direction away from the capsule in the activated state.

* * * * *